(12) United States Patent
Martin et al.

(10) Patent No.: US 6,825,335 B1
(45) Date of Patent: Nov. 30, 2004

(54) SYNTHETIC FATTY ACID DESATURASE GENE FOR EXPRESSION IN PLANTS

(75) Inventors: Charles E. Martin, Somerset, NJ (US); Andrew Mitchell, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/763,331

(22) PCT Filed: Aug. 24, 1999

(86) PCT No.: PCT/US99/19443

§ 371 (c)(1),
(2), (4) Date: May 30, 2001

(87) PCT Pub. No.: WO00/11012

PCT Pub. Date: Mar. 2, 2000

Related U.S. Application Data
(60) Provisional application No. 60/097,586, filed on Aug. 24, 1998.

(51) Int. Cl.$^7$ .................. C12N 15/29; C12N 15/53; C12N 15/82; C12N 15/31; A01H 5/00
(52) U.S. Cl. .................. 536/23.74; 536/23.1; 536/23.2; 435/183; 435/189; 800/281
(58) Field of Search .................. 536/23.1, 23.2, 536/23.7, 23.74; 435/189, 69.1, 69.9, 183; 800/278, 281; 530/350, 820, 824

(56) References Cited

U.S. PATENT DOCUMENTS

| | | | | |
|---|---|---|---|---|
| 5,057,419 A | | 10/1991 | Martin et al. | 435/134 |
| 5,380,831 A | | 1/1995 | Adang et al. | 536/23.71 |
| 5,500,365 A | * | 3/1996 | Fischoff et al. | 435/240.4 |

FOREIGN PATENT DOCUMENTS

| EP | 0 359 472 A2 | 3/1990 |
|---|---|---|
| WO | WO 90/10076 | 9/1990 |
| WO | WO 99/50430 | 10/1999 |

OTHER PUBLICATIONS

Mazier M. et al. Biotechnology Annual Review, 1997, pp. 313–347.*
Iannocone R. et al. Plant Molecular Biology, 1997, vol. 34, pp. 485–496.*
Mitchell A. et al. J. of Biol. Chem., Dec. 15, 1995; vol. 270, No. 50; pp. 29766–29772.*
Choudhary, M.L. et al., "*Agrobacterium* Mediated Transformation of *Petunia Hybrida* with Yeast DELTA–9 Fatty Acid Desaturase", *Journal of Plant Growth Regulation*, 1994, 15, 113–116, XP–002089854.
Ishizaki–Nishizawa, O. et al., "Low–Temperature Resistance of Higher Plants is SIgnificiantly Enhanced by a Nonspecific Cyanobacterial Desaturase", *Nature Biotechnology*, 1996, 14(1), 1003–1006, XP 002057130.

Vemula, M. et al., "Mechanisms of mRNA Stability Regulation in OLE1, A Delta 9 Desaturase in Saccharomyces", *FASEB Journal*, 1998, 12(8), 1282, XP009010847.
Dalphin, M.E., et al., The translational signal database, TransTerm: more organisms, complete genomes. Nucleic Acids Research 25:246–247 (1997).
Fox, B.G. et al., Stearoyl–acyl carrier protein $\Delta^9$ desaturase from *Ricinus communis* is a diiron–oxo protein. Proc. Natl. Acad. Sci. USA 90:2486–2490 (1993).
Grayburn, W.S. et al., Fatty Acid Alteration By A $\Delta 9$ Desaturase In Transgenic Tobacco Tissue. Bio/Technology 10:675–678 (1992).
Hamada, T. et al., Modification of fatty acid composition by over– and antisense–expression of a microsomal omega–3 fatty acid desaturase gene in transgenic tobacco. Transgenic Research 5:115–121 (1996) (abstract only).
Hamada, T. et al., cDNA Cloning of a Wounding–Inducible Gene Encoding a Plastid ω–3 Fatty Acid Desaturase from Tobacco. Plant Cell Physiol. 37:606–611 (1996).
Hebsgaard, S.M. et al., Splice site predictiOn in *Arabidopsis thaliana* pre–mRNA by combining local and global sequence information. Nucleic Acids Research 24:3439–3452 (1996).
Heppard, E.P. et al., Developmental and Growth Temperature Regulation of Two Different Microsomal ω–6 Desaturase Genes in Soybeans. Plant Physiol. 311–319 (1996).
Hugly, S. et al., Enhanced Thermal Tolerance of Photosynthesis and Altered Chloroplast Ultrastructure in a Mutant of *Arabidopsis* Deficient in Lipid Desaturation. Plant Physiol. 90:1134–1142 (1989).
Kozak, M., Structural Features in Eukaryotic mRNAs That Modulate the Initiation of Translation. The Journal of Biological Chemistry 266:19867–19870 (1991).
McDonough, V.M. et al., Specificity of Unsaturated Fatty Acid–regulated Expression of the *Saccharomyces cerevisiae* OLE1 Gene. The Journal of Biological Chemistry 267:5931–5936 (1992).
Mitchell, A.G. and Martin, C.E., A Novel Cytochrome $b_5$–like Domain Is Linked to the Carboxyl Terminus of the *Saccharomyces cerevisiae* $\Delta$–9 Fatty Acid Desaturase. The Journal of Biological Chemistry 270:29766–29771 (1965).
Murata, N. and Wada, H., Acyl–lipid desaturases and their importance in the tolerance and acclimatization to cold of cyanobacteria. Biochem J. 308–1–8 (1995).

(List continued on next page.)

Primary Examiner—David T. Fox
Assistant Examiner—Russell Kallis
(74) Attorney, Agent, or Firm—Woodcock Washburn LLP

(57) ABSTRACT

A synthetic fatty acid desaturase gene for expression in a multicellular plant is provided. The gene comprises a desaturase domain and a cyt $b_5$ domain, and is customized for expression in a plant cytoplasm. Methods for designing and making a synthetic fatty acid desaturase gene customized for expression in a plant cytoplasm are also provided.

11 Claims, 2 Drawing Sheets

OTHER PUBLICATIONS

Oh, C. et al., *ELO2* and *ELO3* Homologues of the *Saccharomyces cerevisiae ELO1* Gene, Function in Fatty Acid Elongation and Are Required for Sphingolipid Formation. The Journal of Biological Chemistry 272:17376–17384 (1997).

Okuley, J. et al., Arabidopsis *FAD2* Gene Encodes the Enzyme That Is Essential for Polyunsaturated Lipid Synthesis. The Plant Cell 6:147–158 (1994).

Polashock, J.J. et al., Expression of the Yeast Δ–9 Fatty Acid Desaturase in *Nicotiana tabacum*. Plant Physiol. 100:894–901 (1992).

Sayanova, O. et al., Expression of a borage desaturase cDNA containing an N–terminal cytochrome $b_5$ domain results in the accumulation of high levels of $\Delta^6$–desaturated fatty acids in transgenic tobacco. Proc. Natl. Acad. Sci. USA 94:4211–4216 (1997).

Schultz, D.J. et al., Expression of a $\Delta^9$ 14:0–acyl carrier protein fatty acid desaturase gene is necessary for the production of a $\omega^5$ anacardic acids found in pest–resistant geranium (*Pelargonium xhortorum*). Proc. Natl. Acad. Sci. USA 93:8771–8775 (1996).

Shah, S. et al., Overexpression of the *FAD3* Desaturase Gene in a Mutant of Arabidopsis. Plant Physiol. 114:1533–1539 (1997).

Shanklin, J. et al., Eight Histidine Residues Are Catalytically Essential in a Membrane–Associated Iron Enzyme, Stearoyl–CoA Desaturase, and Are Conserved in Alkane Hydroxylase and Xylene Monooxygenase. Biochemistry 33:12787–12794 (1994).

Shanklin, J. et al., Mössbauer studies of alkane ω–hydroxylase: Evidence for a diiron cluster in an integral–membrane enzyme. Proc. Natl. Acad. Sci. USA 94:2981–2986 (1997).

Shaw, G. and Kamen, R., A Conserved AU Sequence from the 3' Untranslated Region of GM–CSF mRNA Mediates Selective mRNA Degradation. Cell 46:659–667 (1986).

Somerville, C. and Browse, J., Plant Lipids: Metabolism, Mutants, and Membranes. Science 252:80–87 (1991).

Stukey, J.E. et al., The *OLE1* Gene of *Saccharomyces cerevisiae* Encodes the Δ9 Fatty Acid Desaturase and Can Be Functionally Replaced by the Rat Stearoyl–CoA Desaturase Gene. The Journal of Biological Chemistry 265:20144–20149 (1990).

Thomas, P.G. et al., Increased thermal stability of pigment–protein complexes of pea thylakoids following catalytic hydrogenation of membrane lipids. Biochimica et Biophysica Acta 849:131–140 (1986).

Wang, C. et al., Changes of Fatty Acids and Fatty Acid–Derived Flavor Compounds by Expressng the Yeast Δ–9 Desaturase Gene in Tomato. J. Agric. Food Chem. 44:3399–3402 (1996).

* cited by examiner

SYNTHETIC FATTY ACID DESATURASE GENE FOR EXPRESSION IN PLANTS

This application claims priority to U.S. Provisional Application No. 60/097,586, filed Aug. 24, 1998, the entirety of which is incorporated by reference herein.

FIELD OF THE INVENTION

This invention relates to the field of genetic engineering, and more particularly to transformation of plants with heterologous fatty acid desaturase genes modified for optimum expression in plants.

BACKGROUND OF THE INVENTION

Several publications are referenced in this application in order to more fully describe the state of the art to which this invention pertains. The disclosure of each of these publications is incorporated by reference herein.

Alteration of fatty acid desaturation in plants is of interest to plant biologists and food scientists alike, due to the influence of unsaturated fatty acids on the health benefits and flavors of foods, as well as the role of these molecules in plant biological processes. For a nation interested in healthy diet, the quality of fats and oils depends on their fatty acid composition, with oils high in monounsaturated fatty acids (e.g., canola, olive) gaining popularity as new health benefits are discovered. Considering the flavors of plant foods, many flavor-producing compounds are derived from peroxidation of unsaturated fatty acids. Thus, efforts are being made to produce plants with increased amounts of unsaturated fatty acids, preferably monounsaturated fatty acids.

In animal and fungal cells, monounsaturated fatty acids are aerobically synthesized from saturated fatty acids by a microsomal Δ-9 fatty acid desaturase that is membrane bound and cytochrome $b_5$-dependent. A double bond is inserted between the 9- and 10-carbons of palmitoyl (16:0) and stearoyl (18:0) CoA to form palmitoleic (16:1) and oleic (18:1) acids. In the reaction mechanism, electrons are transferred from NADH-dependent cytochrome $b_5$ reductase, via the heme-containing cytochrome $b_5$ (Cyt $b_5$) molecule, to the Δ-9 fatty acid desaturase. The major form of cytochrome $b_5$ in animal, fungal and plant cells exists as an independent protein molecule that is anchored to the membrane by a short, carboxyl terminal, hydrophobic stretch of amino acids. The carboxyl terminal anchor orients the heme group of the Cyt $b_5$ on the membrane surface and allows it to translationally diffuse across the surface of the membrane. This property of lateral mobility allows this form of cytochrome $b_5$ to participate as an electron donor to a number of different proteins that catalyze a variety metabolic reactions on the membrane surface, including fatty acid desaturases, various sterol biosynthetic enzymes and a variety of cytochrome P450 mediated reactions. While this contributes to the versatility of Cyt $b_5$ as an electron donor, it also implies that the major form of cytochrome $b_5$ shuttles between its redox partners by translational diffusion across the surface of the membrane (Strittmatter and Rogers, Proc. Natl. Acad. Sci. USA, 72: 2658–2661, (1975; Lederer, Biochimie 76: 674–692, 1994). Furthermore, this mechanism suggests that an independent, membrane bound cytochrome $b_5$ molecule can potentially limit the rate of the metabolic reaction, depending on its abundance, its location on the membrane surface, its proximity to the electron acceptor, and the rate at which it can move and orient itself to the acceptor on the membrane surface.

In plants, unsaturated fatty acids are formed and incorporated into complex lipids in two distinct cellular compartments. De novo fatty acid synthesis occurs almost exclusively in the plastids, producing the saturated species 16:0-ACP (acyl carrier protein) and 18:0-ACP. 18:1-ACP is formed from 18:0-ACP in the plastid by a soluble, ferredoxin-dependent Δ-9 desaturase. These fatty acids are then shunted into one of two routes—a plastid-localized "procaryotic" pathway or a cytosolic/ER (endoplasmic reticulum) "eucaryotic" pathway—for further modification and acylation into glycerolipids (Somerville and Browse, Science 252: 80–87, 1991). The acyl ACPs that are shunted into the prokaryotic pathway remain within the plastid and are used for the synthesis of phosphatidic acid and further conversion to chloroplast glycerolipids. The fatty acyl groups of those lipids may be further desaturated by plastid desaturases that also use ferrodoxin as the electron donor.

Acyl-ACPs that are shunted into the eukaryotic pathway are converted to free fatty acids, transported across the chloroplast membrane into the cytoplasm where they are converted to acyl CoA thioesters by acyl CoA synthetase. Those fatty acids are then converted to cytoplasmic/ER phosphatidic acid which can then be converted to membrane glycerophospholipids, or storage lipids, in the form of triacylglycerols and sterol esters that are the major components of plant oils.

Most polyunsaturated 18-carbon plant fatty acids appear to be formed in the cytosol by the ER-bound desaturases (Table 1). Once the 18:1 fatty acid is incorporated into phospholipid, an ER-bound desaturase can catalyze the formation of a Δ-12 double bond in the fatty acyl chain to form Δ-9,12 18:2. Other ER bound desaturase enzymes can act on 18:2 to introduce a Δ-15 double bond to form Δ9,12,15 18:3. These desaturase are thought to be similar to animal and fungal desaturases because they are membrane bound and appear to require a cytochrome $b_5$-mediated electron transport chain.

TABLE 1

| Plant | Gene | Desaturase Type | Primary Activity | b5 chimera | Reference |
|---|---|---|---|---|---|
| Arabidopsis | FAD2 | Δ12, microsomal | 18:1->18:2 | no | Okuley J. et al. Plant Cell 6: 147–158, 1994 |
| Arabidopsis | FAD3 | Δ15, microsomal | 18:2->18:3 | no | Shah S. & Z. Xin, Plant Physiol. 114: 1533–1539, 1997 |
| Nicotiana tabacum | NtFAD3 | Δ15, microsomal | 18:2->18:3 | no | Hamada T. et al. Plant & Cell. Physiol. 37: 606–611, |

TABLE 1-continued

| Plant | Gene | Desaturase Type | Primary Activity | b5 chimera | Reference |
|---|---|---|---|---|---|
| | | | | | 1996, Hamada T. et al. Transgenic Res. 5: 115–121, 1996 |
| Soybean | FAD 2-1 | Δ12, microsomal, developing seeds | 18:1-> 18:2 | no | Heppard E. P. et al. Plant Physiol. 110: 311–319, 1996 |
| Soybean | FAD 2-2 | Δ12, microsomal developing seeds and vegetative tissues | 18:1->18:2 | no | Heppard, E. P. et al. 1996, supra |
| Borage | | Δ-6 | 18:2 (9, 12)-18:3 (6, 9, 12) | yes, N-terminal | Sayanova et al. Proc. Natl. Acad. Sci. USA 94: 4211–4216, 1997 |

The conversion of saturated fatty acyl chains to monounsaturated species in plants appears to be confined to the chloroplasts. No Δ-9 desaturase activity has been identified in the cytoplasm or endoplasmic reticulum of plants. The soluble plant chloroplast Δ-9 desaturase is highly specific for 18:0-ACP as a substrate and does not desaturate 16:0-ACP (Somerville and Browse, supra). As a result, only a small amount of 16:1 is present in most higher plants, while the pool of 16:0 is concomitantly larger due to its disfavor as a substrate for the plant desaturase. By comparison, a larger amount of 18:1 is found in higher plant cells, with a correspondingly lesser amount of 18:0. Thus, for the purpose of increasing the concentration of mono-unsaturated lipids in a plant, the 16:0 fatty acid constitutes a significant pool of available substrate that is under-utilized by the endogenous plant desaturase.

In contrast to the plant Δ-9 desaturase, fungal and animal Δ-9 desaturases efficiently convert a wide range of saturated fatty acids with differing hydrocarbon chain lengths to monounsaturated fatty acids. The *Saccharomyces cerevisiae* enzyme, for example, efficiently desaturates even and odd chain fatty acyl CoA substrates from 13 carbons to 19 carbons in length. A broad functional homology exists among various Cyt $b_5$-dependent desaturases, as evidenced, for example, by the successful expression of the rat Δ-9 desaturase in yeast (Stukey et al., J. Biol. Chem. 2: 20144–20149, 1990).

The rat and yeast Δ-9 desaturase genes have been expressed in plants: both the rat and the yeast genes have been expressed in tobacco (Grayburn et al., BioTechnology 10: 675–678, 1992 (rat); Polashock et al., Plant Physiol. 100: 894–901, 1992 (yeast), and the yeast gene has also been expressed in tomato (Wang et al., J. Agric. Food Chem. 44: 3399–3402, 1996). The yeast Δ-9 desaturase has been shown to function in tobacco and tomato, leading to increases in the level of monounsaturated fatty acids (both 16:1 and 18:1) and other compounds derived from monounsaturated fatty acids (e.g., polyunsaturated fatty acids, hexanal, 1-hexanol, heptanal, trans-2-octenal) (Polashock et al., supra; Wang et al; supra) . Expression of the rat desaturase also led to an increase in monounsaturated 16- and 18-carbon fatty acids (Grayburn et al., supra).

From the foregoing, it can be seen that transgenic plants expressing animal or fungal Δ-9 desaturase genes can be improved in their unsaturated fatty acid composition by virtue of the activity of the foreign enzyme. Of further advantage, it has recently been discovered that some fungal Δ-9 desaturases (e.g., *Saccharomyces cerevisiae*) are fusion proteins comprising an intrinsic Cyt $b_5$ domain (Mitchell & Martin, J. Biol. Chem. 270: 29766–29772, 1995). When this gene is expressed, sufficient Cyt $b_5$ is produced to drive the desaturase reaction at an optimum level and is not dependent on existing plant Cyt $b_5$. The known animal Δ-9 desaturases do not contain this fused Cyt $b_5$ motif and must rely on independently-produced Cyt $b_5$ to provide the electrons for the reactions.

Though fungal or animal Δ-9 desaturases (e.g. the *S. cerevisiae* desaturase or the animal desaturases) may be expressed and functional in certain plants, their expression is likely less than optimal in plants, and expression may not even be possible in other plant species, due to several factors, including differences in codon usage and codon preference in plants as compared to fungi, and among different plant species and the presence of cryptic intron splicing signals, among others. All of these factors can lead to poor expression, or no expression, of a non-plant foreign gene in a plant cell.

Accordingly, in order to make use of non-plant fatty acid desaturases, particularly those such as the *S. cerevisiae* Δ-9 desaturase comprising an internal Cyt $b_5$ motif, a need exists to design modified desaturase-encoding DNA molecules that are customized for expression in plant cells and specific plant tissues. It would be of even greater advantage to optimize such modified DNA molecules for expression in particular plant species, such as those that are grown and harvested primarily for oils.

SUMMARY OF THE INVENTION

According to one aspect of the invention, a synthetic fatty acid desaturase gene for expression in a multi-cellular plant is provided, the gene comprising a desaturase domain and a Cyt $b_5$ domain, wherein the gene is customized for expression in a plant cytoplasm. In one embodiment, the synthetic gene is customized for expression in a monocotyledonous plant. In another embodiment, the synthetic gene is customized for expression in a dicotyledonous plant. In a preferred embodiment, the synthetic gene is customized for expression in a plant genus selected from the group consisting of Arabidopsis, Brassica, Phaeseolus, Oryza, Olea, Elaeis (Oil Palm) and Zea.

In a preferred embodiment of the invention, the desaturase is a cytosolic Δ-9 desaturase. The *Saccharomyces cerevisiae* Δ-9 desaturase is particularly preferred.

In another embodiment of the invention, the synthetic gene is customized from a naturally occurring gene comprising both a desaturase domain and a cyt $b_5$ domain. Alternatively, the synthetic gene is a chimeric gene comprising a desaturase domain and a heterologous cyt $b_5$ domain.

In another embodiment, the synthetic gene is customized from a naturally occurring gene such that the synthetic gene and the naturally occurring gene encode an identical amino acid sequence. Alternatively, the synthetic gene is customized from a naturally occurring gene such that the synthetic gene and the naturally occurring gene encode a similar and functionally conserved amino acid sequence.

In another embodiment, a naturally occurring or a synthetic gene is customized so that specific amino acid modification are made to enhance the function of the encoded protein. Examples of such modifications include changing amino acids that are subjected to phosphorylation or other post-translational modifications that may alter or regulate the activity of the Δ-9 desaturase enzyme.

In another embodiment of the invention, elements of a naturally occurring or a synthetic desaturase gene that are not essential for enzymatic function are replaced or linked with elements derived from plant ER lipid biosynthetic genes that are normally expressed in maturing seeds or other plant tissues. The improved expression of the modified gene produced by the inclusion or substitution of plant DNA sequences in the synthetic gene will result from native plant signal or control elements in those sequences that affect desaturase gene expression at one or more levels.

According to another aspect of the invention, a method is provided for constructing and customizing a bifunctional desaturase/cyt $b_5$ encoding gene for expression in the cytosol of a multicellular plant. The method comprises (a) providing a DNA molecule comprising a desaturase-encoding moiety operably linked to a cyt $b_5$-encoding moiety, said DNA molecule producing the bifunctional polypeptide in a non-customized form; (b) back-translating the polypeptide sequence using preferred codons for expression in a multicellular plant, thereby producing a back-translated nucleotide sequence; (c) analyzing the back-translated nucleotide sequence for features that could diminish or prevent expression in the plant cytoplasm, including, optionally (1) probable intron splice sites (characterized by T-rich regions); (2) plant polyadenylation signals (e.g., AATAAA); (3) polymerase II termination sequence (e.g., $CAN_{(7-9)}AGTNNAA$, where N is any nucleotide); (4) hairpin consensus sequences (e.g., UCUUCGG); and (5) the sequence-destabilizing motif ATTTA; (d) modifying the analyzed sequence to correct or remove the features that could diminish or prevent expression in the plant cytoplasm; and, optionally, (e) introducing desirable cloning features, such as restriction sites, into the sequence in a manner that does not materially affect the desired codon usage or final polypeptide sequence.

The method set forth above may be adapted by incorporating into the customized gene one or more genomic segments from plant desaturase or other ER lipid biosynthetic genes, which are determined to further optimize gene expression in plants. This method comprises (1) identifying cDNA sequences that have potential to comprise such beneficial elements, (2) creating yeast vectors expressing desaturase genes modified to contain these elements, (3) testing the vectors in a yeast expression system, (4) isolating regions from genomic DNA that are homologous to the beneficial cDNA elements, and (6) using them to construct chimeric or hybrid synthetic genes that produce functional and highly efficient desaturase activities in plant tissues.

Other features and advantages of the present invention will be better understood by reference to the drawings, detailed description and examples that follow.

DETAILED DESCRIPTION OF THE INVENTION

I. Definitions

Figure 1:
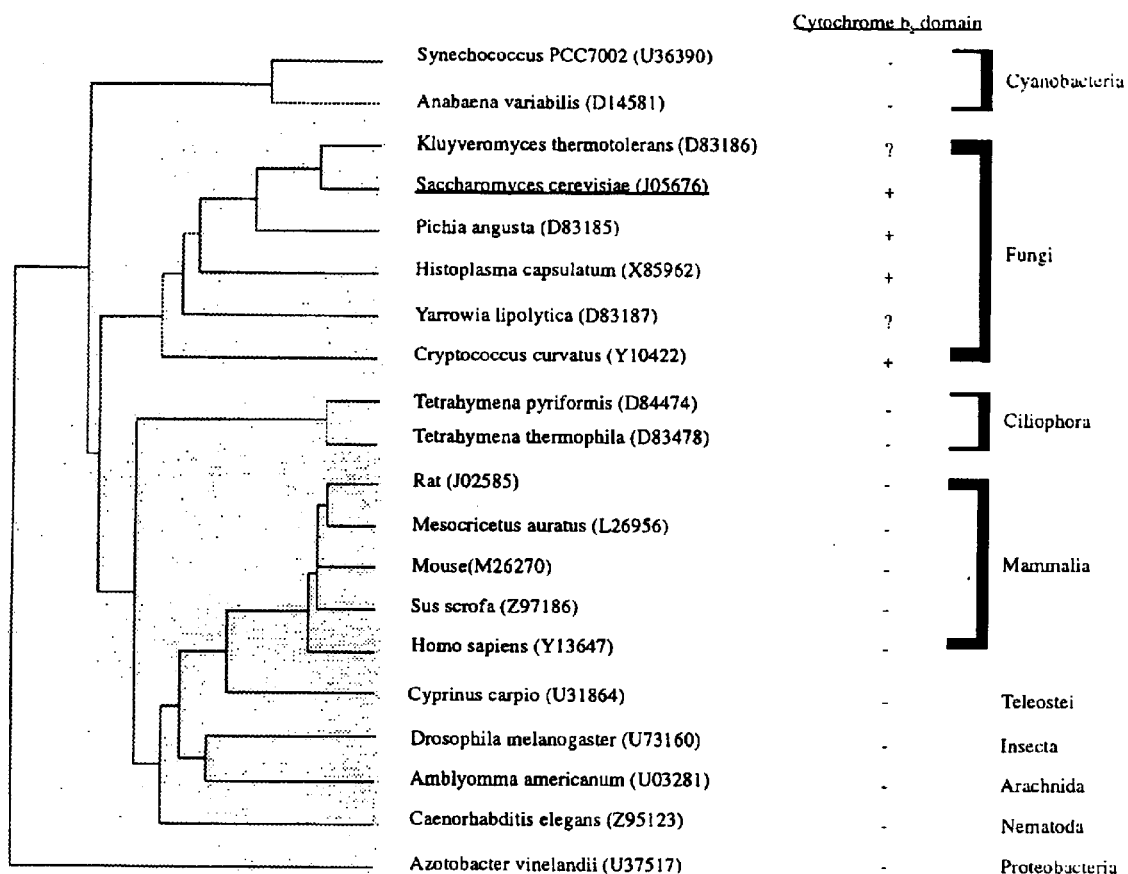
FIG. 1. GCG Pileup comparison of stearoyl-CoA desaturase protein sequences. Sequences containing a Cyt $b_5$ domain are indicated with a +; sequences lacking a Cyt $b_5$ domain are indicated with a –; sequences still in question are indicated with a ?.

Various terms relating to the biological molecules of the present invention are used herein above and also throughout the specifications and claims.

The term "promoter region" refers to the 5' regulatory regions of a gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1999.

This invention provides synthetic DNA molecules (sometimes referred to herein as "synthetic genes") that encode a fatty acid desaturase useful for modifying the fatty acid composition of a plant. The DNA molecules describe in accordance with this invention are superior to DNA molecules currently available for this purpose, in two important respects: (1) they encode a dual-domain polypeptide (sometimes referred to herein as a "bifunctional polypeptide or protein"), one domain being the fatty acid desaturase, and the other domain being cytochrome $b_5$, a protein required to support the electron transfer events that enable the desaturase to function; and (2) they are customized for expression in the cytosol of plant cells, and further customized for expression in particular selected plant species.

Design of synthetic genes of the present is invention is accomplished in two broad steps. First, the two components (the desaturase-encoding component and the Cyt $b_5$-encoding component) are selected and linked together, if they do not occur together naturally. Second, the DNA molecule is optimized for expression in the cytosol of a plant cell, or further for expression in a particular plant species, or group of species.

With regard to the first step, it should be noted that several fungal, animal and plant species, including yeast, are now known to contain naturally-occurring genes encoding dual-domain cytoplasmic fatty acid desaturases. As mentioned above, the yeast and rat Δ-9 desaturase genes have been expressed and shown to function in plants. However, prior to the present invention, it was not appreciated that the bifunctional yeast desaturase offers a significant advantage over the single-function animal desaturase in plant cells, where the requisite Cyt $b_5$ is available only in small amounts, and the yeast protein can provide its own supply of Cyt $b_5$.

With regard to the second step—optimization for expression in the plant cytosol—it was discovered in accordance with the present invention that a non-plant desaturase-encoding gene, such as the yeast OLE 1, though expressed in some plants, may not be optimally expressed in those plants. Furthermore, the inventors have found that the yeast gene is poorly expressed in other plant species, thus highlighting the advantages obtainable by optimizing such a gene for expression in a plant cell.

Sections II–IV below describe in detail how to design and use the synthetic genes of the present invention. To the extent that specific materials are mentioned, it is merely for purposes of illustration and is is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al.") are used.

II. Design and Construction of the Synthetic DNA Molecules

A. Selection of component DNA segments

This invention contemplates the use of the following source DNAs, which are thereafter modified for expression in plants, if necessary:

1. naturally occurring genes or cDNAs that encode dual domain polypeptides comprising a desaturase domain and a Cyt $b_5$ domain;

2. chimeric genes in which a desaturase-encoding sequence from one source (e.g., the desaturase domain of a dual domain fungal Δ-9 desaturase, or the single domain rat desaturase), is linked to a Cyt $b_5$-encoding sequence from a different source (e.g., a plant);

3. chimeric genes in which a sequence that encodes a fragment of a naturally occurring plant Cyt $b_5$ (e.g. the heme binding fold, or residues that comprise the electron donor or acceptor sites, or residues that act as membrane targeting or retention signals, or residues that act to stabilize the protein in the plant cytoplasmic environment) is substituted for homologous regions in the cytochrome $b_5$ domain of a dual domain polypeptide such as the yeast Δ-9 desaturase; and 4. chimeric genes in which elements that encode the essential enzymatic domains from one source (e.g. a native or synthetic gene derived from a fungal Δ-9 desaturase) are linked to elements derived from native plant desaturases that enhance transcription, mRNA processing, mRNA stability, protein folding and maturation, membrane targeting or retention, or protein stability.

Naturally occurring genes or cDNAs that encode dual domain desaturase/Cyt $b_5$ proteins have been identified in several fungal species, including *Saccharomyces cerevisiae, Pichia augusta, Histoplasma capsulatum* and *Cryptococcus curvatus* (See FIG. 1). Naturally occurring genes or cDNA=s that encode independent, diffusible Cyt $b_5$ proteins have been identified in several plant species, including *Nicotiana tabacum* (tobacco), *Oryza sativa* (rice), *Cuscuta reflexa* (southern Asian dodder), *Arabidopsis thaliana, Brassica oleracea* and *Olea europaea* (olive). A N-terminal Cyt $b_5$ domain of a Δ-6 desaturase has also been identified in the plant *Borago officinalis*, and in the *Saccharomyces cerevisiae* FAH1 gene that encodes a very long chain fatty acid hydroxylase. Genes or cDNAs from these species, as well as DNA from any other species identified in the future as encoding such a dual domain protein, are contemplated for use in the synthetic genes of the present invention.

In a preferred embodiment, the yeast OLE1 gene is used. This embodiment is described in detail in Example 1.

The second strategy involves linking a DNA segment encoding a fatty acid desaturase from one source with a Cyt $b_5$ domain from another source. In a preferred embodiment, this chimeric gene is fashioned after the naturally-occurring dual function genes discussed above. That is, the Cyt $b_5$ domain and the desaturase domain are situated in the same positions respective to each other as is found in the naturally occurring genes (see, e.g., Mitchell & Martin, J. Biol. Chem. 270: 29766–29772, 1996).

The chimeric dual-domain proteins of the invention are prepared by recombinant DNA methods, in which DNA sequences encoding each domain are operably linked together such that upon expression, a fusion protein having the desaturase and Cyt $b_5$ functions described above is produced. As defined above, the term "operably linked" means that the DNA segments encoding the fusion protein are assembled with respect to each other, and with respect to an expression vector in which they are inserted, in such a manner that a functional fusion protein is effectively expressed. The selection of appropriate promoters and other 5' and 3' regulatory regions, as well as the assembly of DNA segments to form an open reading frame, employs standard methodology well. known to those skilled in the art.

Thus, preparing the chimeric DNAs of the invention involves selecting DNA sequences encoding each of the aforementioned components and operably linking the respective sequences together in an appropriate vector. The sequences are thereafter expressed to produce the dual-function protein.

Genes or cDNAs that encode single-function cytoplasmic Δ-9 fatty acid desaturases have been identified in a diverse array of procaryotic and eucaryotic species, including insects, fungi and mammals, but not plants (FIG. 1). Genes or cDNAs from any of these species, as well as DNA from any other species identified in the future as encoding a fatty acid desaturase, are contemplated for use in the synthetic genes of the present invention.

In preferred embodiments, desaturase-encoding genes from eucaryotes, most preferably fungi or mammals, are used. In a particularly preferred embodiment, a DNA encoding the rat stearoyl CoA desaturase is used. This DNA has been successfully expressed in tobacco, and accordingly is expected to be useful as part of a chimeric desaturase/Cyt $b_5$ gene of the present invention.

Genes or cDNAs that encode Cyt $b_5$ proteins have also been identified in a diverse array of eukaryotic species, including insects, fungi, mammals and plants. Genes or cDNAs from any of these species, as well as DNA from any other species identified in the future as encoding a Cyt $b_5$ protein, are contemplated for use in the synthetic genes of the present invention.

Figure 2:
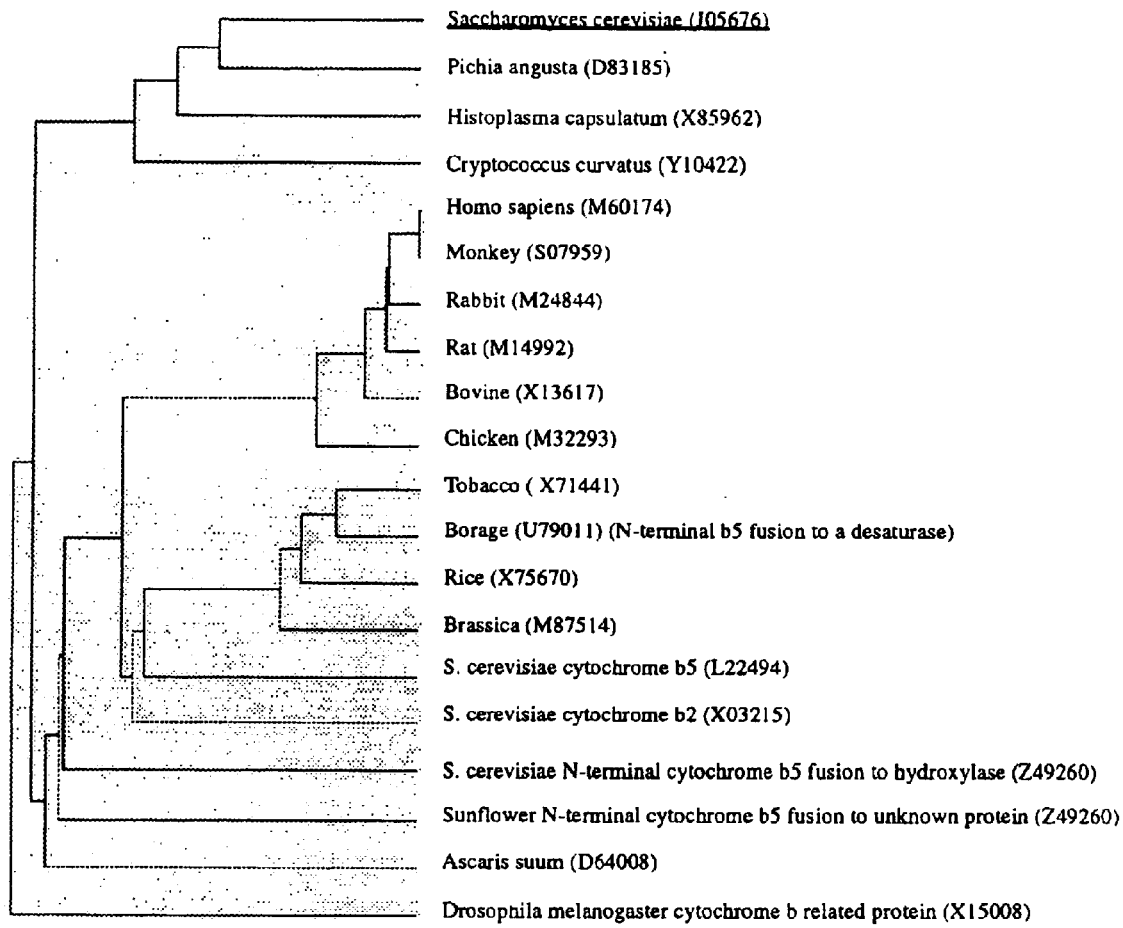
FIG. 2. GCG Pileup comparison of Cytochrome $b_5$ protein sequences.

In preferred embodiments, Cyt $b_5$-encoding genes or cDNAs from plants are used. These DNAs are preferred because they naturally comprise the codon usage preferred in plants, so require little, if any, of the modification steps described below for non-plant genes. Particularly preferred, if available, are Cyt $b_5$-encoding DNAs from the same plant species (or group of species) to be transformed with the chimeric gene. For instance, synthetic chimeric genes constructed for transformation of Brassica species might comprise a stearoyl CoA-encoding domain from rat and a Cyt $b_5$ domain from Brassica (see FIGS. 1 and 2 for specific sources). This chimeric DNA would require optimization for expression in Brassica only in the desaturase domain.

With respect to the naturally-occurring dual domain-encoding genes, as well as the chimeric genes discussed above, it will be appreciated that the DNA molecules can be prepared in a variety of ways, including DNA synthesis, cloning, mutagenesis, amplification, enzymatic digestion, and similar methods, all available in the standard literature. Additionally, certain DNA molecules can be obtained by access to public repositories, such as the American Type Culture Collection. Alternatively, DNA molecules that are not readily available, and/or for which sequence information is not available, can be isolated from biological sources using standard hybridization methods and homologous probes that are available.

B. Optimization for expression in plants

The second step in designing the synthetic DNA molecules of the invention is to customize (i.e. optimize) their sequence for expression in the plant cytoplasm. This is accomplished by performing one or more of the steps listed below on the coding sequence of the above described non-plant (or chimeric) desaturase/Cyt $b_5$-encoding DNA molecules.

1. From the peptide sequence encoded by the DNA, back translate using an appropriate plant codon usage table, making certain in particular that the most preferred translation termination codon is used.

2. Visually, or with the aid of computer software, analyze the back-translated nucleotide sequence for features that could diminish or prevent expression in the plant cytoplasm. Such features include: (1) probable intron splice sites (characterized by T-rich regions); (2) plant polyadenylation signals (e.g., AATAAA); (3) polymerase II termination sequence (e.g., $CAN_{(7-9)}AGTNNAA$, where N is any nucleotide); (4) hairpin consensus sequences (e.g., UCUUCGG); and (5) the sequence-destabilizing motif ATTTA (Shah & Kamen, Cell 4: 659–667, 1986). These features have been described in the art (U.S. Pat. No. 5,500,365 to Fischhoff et al.; U.S. Pat. No. 5,380,831 to Adang et al.).

3. Modify the back-translated sequence in light of any "problem" sequences identified in step 2. Note that this step may require the introduction of codons that are not the most preferred, but instead are second or third-most preferred, in order to eliminate the more problematic sequences identified in step 2.

4. Introduce desirable cloning features, such as restriction sites, into the sequence in a manner that does not materially affect the desired codon usage or final polypeptide sequence.

The aforementioned optimization procedure can be performed so that the final polypeptide sequence is identical to the initial polypeptide sequence, even though the underlying nucleotide sequence has been modified. This is a preferred embodiment of the invention. However, it is entirely feasible to modify the initial sequence such that the final sequence is not identical to the initial sequence, either by virtue of amino acid substitutions, insertions or deletions. The more that is known about the structure/function relationship in a particular desaturase protein, the more liberties can be taken in modifying the protein sequence during the DNA optimization process. For instance, the present inventors have shown that the entire "coiled coil" domain of the yeast OLE1 gene can be deleted, and the protein remains functional. Thus, it appears that OLE1 can tolerate significant modification in the encoded protein without losing its biological activity.

Codon usage tables for a variety of plants, including general plant codon usage tables, tables for dicots, tables for monocots, and tables for particular species, are widely available. Some of these are reproduced in Example 1 below. One good location to access such tables is the website:

http://biochem.octago.ac.nz.800/Transterm/codons.html.

In an exemplary embodiment of the present invention, the above process is applied to the coding sequence of the yeast OLE1 gene, which encodes a cytoplasmically expressed dual-domain protein comprising a Δ-9 fatty acid desaturase domain and a Cyt $b_5$ domain. Optimization of the OLE1 gene for expression in Arabidopsis and related species is described in detail in Example 1.

In another preferred embodiment, the coding sequence of the rat stearoyl CoA desaturase is modified for expression in plants according to the methods described above. The modified sequence is operably linked to a coding sequence for a Cyt $b_5$ domain, preferably from a plant, and most preferably from Brassica. In this regard, it has been shown that expression of this rat desaturase in tobacco produces a functional protein that increases the 16:1 fatty acid content of plant tissues. Splice site prediction analysis of the rat desaturase reveals that there are no plant intron-like sequences within the open reading frame. However, codon usage analysis reveals that this desaturase possesses a number of codons that are not optimal for expression in plants, particularly Arabidopsis or Brassica.

In another preferred embodiment, the protein coding sequences of the modified vectors described above are further modified to increase desaturase activity. This is done by altering specific amino acids in the encoded protein that control desaturase activity through post-translational modifications. These modifications are presumed to increase the level of desaturase activity in the host plant by stabilizing the desaturase protein or by increasing catalytic activity of the desaturase. Post translational modifications such as protein phosphorylation or dephosphorylation have been shown to alter activity of a number of enzymes by a number of different mechanisms. These include increasing or decreasing enzyme activity or protein stability, or changing the intracellular location of the enzyme. An examination of a wide range of Δ-9 desaturase enzymes reveals the existence of a number of highly conserved potential phosphorylations sites that could serve as sequences that regulate desaturase activity. These are shown in bold face on the pile-up diagram in FIG. 3 and are summarized in Table 1 of Example 3. The high degree of homology between these sites suggests that these sequences may also be recognized by host plant phosphorylating or dephosphorylating enzymes. If phosphorylation of an amino acid within one of the sites increases the activity of the desaturase, the nucleic acid sequence corresponding to that amino acid can be altered to encode a negatively charged amino acid at that site to permanently increase the activity of the protein in the host. If phosphorylation of an amino acid within the site reduces the activity of the desaturase enzyme, the nucleic acid sequence can be altered to replace that amino acid with a neutral amino acid that will permanently increase the activity of the enzyme.

In another preferred embodiment, elements of the genes in the modified vectors described above are further modified and improved by the linkage or substitution of sequences derived from native plant ER lipid biosynthetic genes. Those sequences contain elements that improve the desaturase activity by increasing the efficiency of gene expression, intracellular protein targeting and/or enzyme stability. This is done by identifying elements of the engineered desaturase gene that can be replaced or linked with elements of a plant gene without significantly affecting the desired activity or specificity of the resulting enzyme. Genes and cDNAs that encode ER lipid biosynthetic enzymes from Brassica, Arabidopsis, *Nicotiana tabacum*, Borage, maize, sunflower and soybeans, as well as similar plant genes from any other species that are identified in the future, are contemplated for use in the synthetic genes of the present invention.

In connection with the aforementioned embodiment, but not limited thereto, it is particularly useful in many cases to pre-test constructs of the invention in a yeast expression system, in order to eliminate constructs that work poorly before taking the more labor- and time-intensive step of testing them in plants. Accordingly, this step may be incorporated into the methods described herein.

III. Construction of Vectors for Transforming Plant Nuclei, and Production of Transgenic Plants Expressing Synthetic Genes of the Invention The synthetic genes of the present invention are intended for use in producing transgenic plants that optimally express a dual-function desaturase/Cyt $b_5$ protein in the cytoplasm of plant cells. Transformation of plant nuclei to produce transgenic plants may be accomplished according to standard methods known in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology*, Weissbach & Weissbach eds., Academic Press, Inc. (1988); *Methods in Plant Molecular Biology*, Schuler & Zielinski, eds., Academic Press, Inc. (1989); *Plant Molecular Biology Manual*, Gelvin Schilperoort, Verma, eds., Kluwer Academic Publishers, Dordrecht (1993); and *Methods in Plant Molecular Biology—A Laboratory Manual*, Maliga, Klessig, Cashmore, Gruissem & Varner, eds., Cold Spring Harbor Press (1994).

The method of transformation depends upon the plant to be transformed. The biolistic DNA delivery method is useful for nuclear transformation, and is a preferred method for practice of this invention. In another embodiment of the invention, Agrobacterium vectors are used to advantage for efficient transformation of plant nuclei.

In a preferred embodiment, the synthetic gene is introduced into plant nuclei in Agrobacterium binary vectors. Such vectors include, but are not limited to, BIN19 (Bevan, Nucl. Acids Res., 12: 8711–8721, 1984) and derivatives thereof, the pBI vector series (Jefferson et al., EMBO J., 6: 3901–3907, 1987), and binary vectors pGA482 and pGA492 (An, Plant Physiol., 81: 86–91, 1986). A new series of Agrobacterium binary vectors, the pPZP family, is preferred for practice of the present invention. The use of this vector family for plant transformation is described by Svab et al. in *Methods in Plant Molecular Biology—A Laboratory Manual*, Maliga, Klessig, Cashmore, Gruissem and Varner, eds., Cold Spring Harbor Press (1994).

Using an Agrobacterium binary vector system for transformation, the synthetic gene of the invention is linked to a nuclear drug resistance marker, such as kanamycin or gentamycin resistance. Agrobacterium-mediated transformation of plant nuclei is accomplished according to the following procedure:

(1) the gene is inserted into the selected Agrobacterium binary vector;

(2) transformation is accomplished by co-cultivation of plant tissue (e.g., leaf discs) with a suspension of recombinant Agrobacterium, followed by incubation (e.g., two days) on growth medium in the absence of the drug used as the selective medium (see, e.g., Horsch et al., Science 227: 1229–1231, 1985);

(3) plant tissue is then transferred onto the selective medium to identify transformed tissue; and (4) identified transformants are regenerated to intact plants.

It should be recognized that the amount of expression, as well as the tissue specificity of expression of the synthetic genes in transformed plants can vary depending on the position of their insertion into the nuclear genome. Such position effects are well known in the art; see Weising et al., Ann. Rev. Genet., 22: 421–477 (1988). For this reason, several nuclear transformants should be regenerated and tested for expression of the synthetic gene.

IV. Uses of the Synthetic Genes and Transgenic Plants Expressing Those Genes The synthetic desaturase genes of the invention and transgenic plants expressing those genes can be used for several agriculturally beneficial purposes. For instance, they can be used in oil-producing crops (e.g., corn, soybean, sunflower, rapeseed) to increase the overall percentages of monounsaturated fatty acids in those oils, thereby improving their health-promoting qualities. In this regard, the production of transgenic rapeseed plants (*Brassica napus*) is of particular interest in this invention. Example 1 describes a synthetic yeast desaturase gene modified for expression in Arabidopsis. Because the codon usage of Brassica is very similar to that of Arabidopsis, it is expected that the synthetic gene described in Example 1 will be as well expressed in Brassica as it is in Arabidcopsis.

Another use for the synthetic genes of the invention is to modify the flavors of certain fruit or vegetable crops. It has already been shown that expression of the un-modified yeast Δ-9 desaturase gene in tomato results in alterations in fatty acid composition and fatty acid-derived flavor compounds (Wang et al., 1996, supra). The synthetic, plant-optimized version of this gene is expected to function similarly, and also to be more efficiently expressed in plant cells.

Another use for the synthetic genes of the invention is to facilitate the formation of omega-5 anacardic acids, a class of secondary compounds derived from the Δ-9 desaturation of 14:0 in pest-resistant geraniums (Schultz et al., Proc. Natl. Acad. Sci. USA, 93: 877–885, 1996). It has been shown that formation of these compounds proceeds from the expression of Δ9 desaturase activity resulting in the formation of Δ9 14:1. Subsequent elongation of these molecules leads to the formation of omega-5 22:1 and 24:1 in the trichome exudate that leads to pest resistance against spider mites and aphids.

Another use for the synthetic genes of the invention are in the modification of membrane lipid fatty acyl composition to alter the properties of the cytoplasmic and plasma membranes of the cell. These may affect functions such membrane associated activities that are associated with membrane functions such as signal transduction, endocytosis or exocytotic events, entry of fungal or viral pathogens into the cell, and temperature or environmentally caused stress that causes physical changes in the fluid properties of the plasma membrane or internal cell membranes. Plants defective in desaturases have been reported (Somerville and Browse, supra). These mutant plants contain higher than normal levels of saturated fatty acids that may lower membrane fluidity under normal growing conditions. Thus the effects of temperature on these plants involved high temperature tolerance as opposed to chilling tolerance. These studies yielded interesting information that has relevance to temperature stress in general. A mutant of Arabidopsis deficient in 16:0 desaturation (Hugly et al, Plant Physiol. 90: 1134–1142) for example, has been shown to appear and grow normally at non-stressful temperatures. Under high temperature conditions, however, the mutant performs better than controls in growth and biosynthetic studies. Higher temperature stability was also noted in pea thylakoids following catalytic hydrogenation (Thoman et al. Biochem. Biophys. Acta 849: 131–140, 1986).

The following examples are provided to describe the invention in greater detail. They are intended to illustrate, not to limit, the invention.

EXAMPLE 1

Modification of the *Saccharomyces cerevisiae* OLE1 Gene for Expression in Arabidopsis and Related Species When introduced into tobacco and tomato plants, the yeast Δ-9 desaturase gene (OLE1) was shown to desaturate palmitate and stearate, thereby reducing the levels of saturated fatty acids in triglycerides (Polashock et al., supra; Wang et al., supra) . However, it was unclear whether optimum expression of the OLE1 gene occurred in those species, and expression in other plant species has been less than optimum. For example, the present inventors have found that the level of expression of the OLE1 gene in tobacco (Polashock, et. al., Plant Physiol. 100:894–901, 1992) and Arabidopsis varies in different plant tissues and is generally poor in tobacco, and Arabidopsis seeds. Similarly, data from other investigators indicate that expression of OLE1 in rapeseed (*Brassica napus*) seeds is also poor (U.S. Pat. No. 5,777,201, to Poutre, et al.).

Differential expression of heterologous genes in plants can be caused by several factors. It is often due to the presence of cryptic intron splicing signals. Thus, it is possible that the multiple banding patterns observed in northern blots of OLE1-transformed tobacco (Polashock et al., supra) are due to splicing of the OLE1 mRNA.

In plants, the mRNA splicing mechanism is less well defined than in mammalian or yeast systems. There is some conservation of the 5' and 3' splicing signals but there is no conserved internal splice signal. However, with the accumulation of plant genomic DNA sequence data, it is now becoming possible to predict with some accuracy where intron splicing will occur (Hebsgaard, S. M., P. G. Korning, N. Tolstrup, J. Engelbrecht, P. Rouze and S. Brunak, Nucleic Acids Research 24(17): 3439–3452, 1996). In fact, computer programs that predict splice sites have now been developed (the "PlantNetGene" server for splice site predictions: http://www.cbs.dtu.dk/NetPlantGene.html). From these sources, it appears that plant introns are typically identified as T rich sequences.

Another factor affecting expression of foreign genes in plants is codon preference. It is now well known that preference for certain codons exist among different phyla, classes, families, genera and species. Accordingly, by modifying a DNA sequence so that it uses codons preferred in a particular organism, expression of that sequence can be optimized.

Other factors affecting the expression of foreign genes in plants include the presence of putative polyadenylation signals, hairpin cleavage consensus motifs, polymerase II termination sequences and the Shaw-Kamen sequence pattern ATTTA.

This example describes the design and construction of "pl-ole1", a modified *Saccharomyces cerevisiae* OLE1 gene optimized for expression in Arabidopsis and other plant species.

The nucleotide sequence of the *Saccharomyces cerevisiae* OLE1 gene coding sequence has been described in U.S. Pat. No. 5,057,419 to Martin et al. (incorporated by reference herein) and is set forth below for convenience as SEQ ID NO:1 (open reading frame starts at +11). The *S. cerevisiae* Δ-9 desaturase amino acid sequence encoded by OLE1 is set forth as SEQ ID NO:2.

I. Design of pl-ole1

To modify OLE1 for optimum expression in plants, the OLE1 sequence was first analyzed for cryptic plant splice signals, using the PlantNetGene server for splice site predictions. This analysis identified a number of "high confidence" intron splice signals in the OLE1 sequence. These are shown below (positions correspond to position numbers in SEQ ID NO:1).

| 5'–3' Position | Strand | Confidence | 5'–3' exon ^ intron |
|---|---|---|---|
| Donor splice site, direct strand: (Start ATG = +1) | | | |
| 397 | + | 1.00 | GCTCTCTCTG ^GTAAAGTACC |
| 1052 | + | 0.85 | CTATTAAGTG ^GTACCAATAC |
| 1074 | + | 1.00 | CCCAACTAAG ^GTTATCATCT |
| Accentor splice site, direct strand: | | | |
| 500 | + | 0.86 | GGTCTCACAG ^ATCTTACTCC |

Next, the CLE1 peptide sequence (SEQ ID NO:2) was back-translated using an *Arabidopsis thaliana* codon usage table, as shown below. Codon usage in Arabidopsis and several other plant species, including *Brassica napus*, *Phaseolus vulgaris* and *Zea mays* is very similar, as can be seen by a comparison with the respective codon usage tables of those species, also shown below (the codon usage table of *Saccharomyces cerevisiae* is shown for comparison; codon usage tables taken from Ahttp://biochem.otago.ac.nz:800/Transterm/codons.html).

| AmAcid | Codon | Number | /1000 | Fraction |
|---|---|---|---|---|
| *Arabidopsis thaliana.* | | | | |
| Gly | GGG | 6027.00 | 10.31 | 0.14 |
| Gly | GGA | 15393.00 | 26.32 | 0.37 |
| Gly | GGT | 14890.00 | 25.46 | 0.35 |
| Gly | GGC | 5654.00 | 9.67 | 0.13 |
| Glu | GAG | 19825.00 | 33.90 | 0.51 |
| Glu | GAA | 18672.00 | 31.93 | 0.49 |
| Asp | GAT | 20862.00 | 35.67 | 0.65 |
| Asp | GAC | 11061.00 | 18.91 | 0.35 |
| Val | GTG | 10414.00 | 17.81 | 0.26 |
| Val | GTA | 5145.00 | 8.80 | 0.13 |
| Val | GTT | 16157.00 | 27.63 | 0.41 |
| Val | GTC | 8156.00 | 13.95 | 0.20 |
| Ala | GCG | 5361.00 | 9.17 | 0.13 |
| Ala | GCA | 10552.00 | 18.04 | 0.25 |
| Ala | GCT | 18782.00 | 32.12 | 0.45 |
| Ala | GCC | 7249.00 | 12.40 | 0.17 |
| Arg | AGG | 6684.00 | 11.43 | 0.22 |
| Arg | AGA | 10280.00 | 17.58 | 0.34 |
| Ser | AGT | 7369.00 | 12.60 | 0.16 |
| Ser | AGC | 6399.00 | 10.94 | 0.14 |
| Lys | AAG | 20436.00 | 34.94 | 0.55 |
| Lys | AAA | 16882.00 | 28.87 | 0.45 |
| Asn | AAT | 11658.00 | 19.93 | 0.47 |
| Asn | AAC | 12987.00 | 22.21 | 0.53 |
| Met | ATG | 14817.00 | 25.34 | 1.00 |
| Ile | ATA | 6571.00 | 11.24 | 0.21 |
| Ile | ATT | 13028.00 | 22.28 | 0.41 |
| Ile | ATC | 11855.00 | 20.27 | 0.38 |
| Thr | ACG | 4346.00 | 7.43 | 0.14 |
| Thr | ACA | 8703.00 | 14.88 | 0.28 |
| Thr | ACT | 10909.00 | 18.65 | 0.36 |
| Thr | ACC | 6720.00 | 11.49 | 0.22 |
| Trp | TGG | 6868.00 | 11.74 | 1.00 |
| End | TGA | 652.00 | 1.11 | 0.44 |
| Cys | TGT | 5641.00 | 9.65 | 0.58 |
| Cys | TGC | 4154.00 | 7.10 | 0.42 |
| End | TAG | 252.00 | 0.43 | 0.17 |
| End | TAA | 591.00 | 1.01 | 0.40 |
| Tyr | TAT | 8052.00 | 13.77 | 0.47 |
| Tyr | TAC | 8965.00 | 15.33 | 0.53 |
| Leu | TTG | 11727.00 | 20.05 | 0.22 |
| Leu | TTA | 6361.00 | 10.88 | 0.12 |
| Phe | TTT | 11703.00 | 20.01 | 0.47 |
| Phe | TTC | 13066.00 | 22.34 | 0.53 |
| Ser | TCG | 4830.00 | 8.26 | 0.10 |
| Ser | TCA | 9033.00 | 15.45 | 0.19 |
| Ser | TCT | 13022.00 | 22.27 | 0.28 |
| Ser | TCC | 6214.00 | 10.63 | 0.13 |
| Arg | CGG | 2531.00 | 4.33 | 0.08 |
| Arg | CGA | 3142.00 | 5.37 | 0.10 |
| Arg | CGT | 5680.00 | 9.71 | 0.19 |
| Arg | CGC | 2100.00 | 3.59 | 0.07 |
| Gln | CAG | 9564.00 | 16.35 | 0.47 |
| Gln | CAA | 10908.00 | 18.65 | 0.53 |
| His | CAT | 7466.00 | 12.77 | 0.58 |
| His | CAC | 5415.00 | 9.26 | 0.42 |
| Leu | CTG | 5669.00 | 9.69 | 0.11 |
| Leu | CTA | 5350.00 | 9.15 | 0.10 |
| Leu | CTT | 14395.00 | 24.61 | 0.27 |
| Leu | CTC | 9751.00 | 16.67 | 0.18 |
| Pro | CCG | 4676.00 | 8.00 | 0.17 |
| Pro | CCA | 9131.00 | 15.61 | 0.33 |
| Pro | CCT | 10732.00 | 18.35 | 0.39 |
| Pro | CCC | 3331.00 | 5.70 | 0.12 |
| *Brassica napus* | | | | |
| Gly | GGG | 730.00 | 11.21 | 0.13 |
| Gly | GGA | 2042.00 | 31.37 | 0.36 |
| Gly | GGT | 1952.00 | 29.99 | 0.35 |
| Gly | GGC | 892.00 | 13.70 | 0.16 |
| Glu | GAG | 2119.00 | 32.55 | 0.55 |
| Glu | GAA | 1764.00 | 27.10 | 0.45 |
| Asp | GAT | 1895.00 | 29.11 | 0.56 |
| Asp | GAC | 1478.00 | 22.70 | 0.44 |
| Val | GTG | 1231.00 | 18.91 | 0.28 |

-continued

| AmAcid | Codon | Number | /1000 | Fraction |
|---|---|---|---|---|
| Val | GTA | 493.00 | 7.57 | 0.11 |
| Val | GTT | 1624.00 | 24.95 | 0.36 |
| Val | GTC | 1124.00 | 17.27 | 0.25 |
| Ala | GCG | 615.00 | 9.45 | 0.13 |
| Ala | GCA | 1167.00 | 17.93 | 0.24 |
| Ala | GCT | 2028.00 | 31.15 | 0.42 |
| Ala | GCC | 1056.00 | 16.22 | 0.22 |
| Arg | AGG | 697.00 | 10.71 | 0.22 |
| Arg | AGA | 996.00 | 15.30 | 0.32 |
| Ser | AGT | 736.00 | 11.31 | 0.15 |
| Ser | AGC | 803.00 | 12.34 | 0.17 |
| Lys | AAG | 2243.00 | 34.46 | 0.55 |
| Lys | AAA | 1817.00 | 27.91 | 0.45 |
| Asn | AAT | 1058.00 | 16.25 | 0.37 |
| Asn | AAC | 1811.00 | 27.82 | 0.63 |
| Met | ATG | 1538.00 | 23.63 | 1.00 |
| Ile | ATA | 669.00 | 10.28 | 0.20 |
| Ile | ATT | 1271.00 | 19.52 | 0.37 |
| Ile | ATC | 1461.00 | 22.44 | 0.43 |
| Thr | ACG | 563.00 | 8.65 | 0.15 |
| Thr | ACA | 1059.00 | 16.27 | 0.28 |
| Thr | ACT | 1154.00 | 17.73 | 0.30 |
| Thr | ACC | 1073.00 | 16.48 | 0.28 |
| Trp | TGG | 798.00 | 12.26 | 1.00 |
| End | TGA | 69.00 | 1.06 | 0.37 |
| Cys | TGT | 517.00 | 7.94 | 0.50 |
| Cys | TGC | 509.00 | 7.82 | 0.50 |
| End | TAG | 33.00 | 0.51 | 0.18 |
| End | TAA | 83.00 | 1.28 | 0.45 |
| Tyr | TAT | 792.00 | 12.17 | 0.38 |
| Tyr | TAC | 1283.00 | 19.71 | 0.62 |
| Leu | TTG | 1051.00 | 16.14 | 0.20 |
| Leu | TTA | 508.00 | 7.80 | 0.09 |
| Phe | TTT | 1003.00 | 15.41 | 0.39 |
| Phe | TTC | 1562.00 | 23.99 | 0.61 |
| Ser | TCG | 475.00 | 7.30 | 0.10 |
| Ser | TCA | 856.00 | 13.15 | 0.18 |
| Ser | TCT | 1147.00 | 17.62 | 0.24 |
| Ser | TCC | 799.00 | 12.27 | 0.17 |
| Arg | CGG | 219.00 | 3.36 | 0.07 |
| Arg | CGA | 297.00 | 4.56 | 0.09 |
| Arg | CGT | 659.00 | 10.12 | 0.21 |
| Arg | CGC | 275.00 | 4.22 | 0.09 |
| Gln | CAG | 1188.00 | 18.25 | 0.50 |
| Gln | CAA | 1168.00 | 17.94 | 0.50 |
| His | CAT | 651.00 | 10.00 | 0.49 |
| His | CAC | 672.00 | 10.32 | 0.51 |
| Leu | CTG | 592.00 | 9.09 | 0.11 |
| Leu | CTA | 579.00 | 8.89 | 0.11 |
| Leu | CTT | 1416.00 | 21.75 | 0.26 |
| Leu | CTC | 1208.00 | 18.56 | 0.23 |
| Pro | CCG | 542.00 | 8.33 | 0.15 |
| Pro | CCA | 1180.00 | 18.13 | 0.33 |
| Pro | CCT | 1281.00 | 19.68 | 0.36 |
| Pro | CCC | 527.00 | 8.10 | 0.15 |
| *Phaseolus vulgaris* | | | | |
| Gly | GGG | 371.00 | 13.30 | 0.15 |
| Gly | GGA | 771.00 | 27.64 | 0.32 |
| Gly | GGT | 817.00 | 29.29 | 0.34 |
| Gly | GGC | 441.00 | 15.81 | 0.18 |
| Glu | GAG | 912.00 | 32.69 | 0.54 |
| Glu | GAA | 767.00 | 27.50 | 0.46 |
| Asp | GAT | 776.00 | 27.82 | 0.55 |
| Asp | GAC | 625.00 | 22.41 | 0.45 |
| Val | GTG | 661.00 | 23.70 | 0.36 |
| Val | GTA | 174.00 | 6.24 | 0.09 |
| Val | GTT | 653.00 | 23.41 | 0.36 |
| Val | GTC | 346.00 | 12.40 | 0.19 |
| Ala | GCG | 180.00 | 6.45 | 0.09 |
| Ala | GCA | 528.00 | 18.93 | 0.26 |
| Ala | GCT | 791.00 | 28.36 | 0.39 |
| Ala | GCC | 553.00 | 19.82 | 0.27 |
| Arg | AGG | 324.00 | 11.61 | 0.29 |
| Arg | AGA | 325.00 | 11.65 | 0.29 |
| Ser | AGT | 317.00 | 11.36 | 0.14 |
| Ser | AGC | 353.00 | 12.65 | 0.15 |

| AmAcid | Codon | Number | /1000 | Fraction |
|---|---|---|---|---|
| Lys | AAG | 1054.00 | 37.78 | 0.60 |
| Lys | AAA | 697.00 | 24.99 | 0.40 |
| Asn | AAT | 555.00 | 19.90 | 0.42 |
| Asn | AAC | 782.00 | 28.03 | 0.58 |
| Met | ATG | 567.00 | 20.33 | 1.00 |
| Ile | ATA | 274.00 | 9.82 | 0.20 |
| Ile | ATT | 539.00 | 19.32 | 0.40 |
| Ile | ATC | 548.00 | 19.65 | 0.40 |
| Thr | ACG | 166.00 | 5.95 | 0.11 |
| Thr | ACA | 362.00 | 12.96 | 0.24 |
| Thr | ACT | 480.00 | 17.21 | 0.32 |
| Thr | ACC | 490.00 | 17.57 | 0.33 |
| Trp | TGG | 342.00 | 12.26 | 1.00 |
| End | TGA | 34.00 | 1.22 | 0.44 |
| Cys | TGT | 145.00 | 5.20 | 0.39 |
| Cys | TGC | 229.00 | 8.21 | 0.61 |
| End | TAG | 22.00 | 0.79 | 0.28 |
| End | TAA | 22.00 | 0.79 | 0.28 |
| Tyr | TAT | 400.00 | 14.34 | 0.40 |
| Tyr | TAC | 597.00 | 21.40 | 0.60 |
| Leu | TTG | 543.00 | 19.47 | 0.24 |
| Leu | TTA | 184.00 | 6.60 | 0.08 |
| Phe | TTT | 458.00 | 16.42 | 0.43 |
| Phe | TTC | 601.00 | 21.55 | 0.57 |
| Ser | TCG | 149.00 | 5.34 | 0.06 |
| Ser | TCA | 416.00 | 14.91 | 0.18 |
| Ser | TCT | 606.00 | 21.72 | 0.26 |
| Ser | TCC | 501.00 | 17.96 | 0.21 |
| Arg | CGG | 71.00 | 2.55 | 0.06 |
| Arg | CGA | 76.00 | 2.72 | 0.07 |
| Arg | CGT | 169.00 | 6.06 | 0.15 |
| Arg | CGC | 158.00 | 5.66 | 0.14 |
| Gln | CAG | 437.00 | 15.67 | 0.48 |
| Gln | CAA | 470.00 | 16.85 | 0.52 |
| His | CAT | 298.00 | 10.68 | 0.46 |
| His | CAC | 355.00 | 12.73 | 0.54 |
| Leu | CTG | 351.00 | 12.58 | 0.15 |
| Leu | CTA | 184.00 | 6.60 | 0.08 |
| Leu | CTT | 569.00 | 20.40 | 0.25 |
| Leu | CTC | 452.00 | 16.20 | 0.20 |
| Pro | CCG | 147.00 | 5.27 | 0.08 |
| Pro | CCA | 694.00 | 24.88 | 0.37 |
| Pro | CCT | 664.00 | 23.80 | 0.36 |
| Pro | CCC | 352.00 | 12.62 | 0.19 |
| *Zea mays* | | | | |
| Gly | GGG | 2466.00 | 15.07 | 0.19 |
| Gly | GGA | 2186.00 | 13.36 | 0.17 |
| Gly | GGT | 2607.00 | 15.93 | 0.20 |
| Gly | GGC | 5499.00 | 33.61 | 0.43 |
| Glu | GAG | 7364.00 | 45.01 | 0.72 |
| Glu | GAA | 2823.00 | 17.25 | 0.28 |
| Asp | GAT | 3425.00 | 20.93 | 0.37 |
| Asp | GAC | 5740.00 | 35.08 | 0.63 |
| Val | GTG | 4365.00 | 26.68 | 0.38 |
| Val | GTA | 916.00 | 5.60 | 0.08 |
| Val | GTT | 2516.00 | 15.38 | 0.22 |
| Val | GTC | 3644.00 | 22.27 | 0.32 |
| Ala | GCG | 3698.00 | 22.60 | 0.24 |
| Ala | GCA | 2517.00 | 15.38 | 0.16 |
| Ala | GCT | 3602.00 | 22.01 | 0.24 |
| Ala | GCC | 5481.00 | 33.50 | 0.36 |
| Arg | AGG | 2500.00 | 15.28 | 0.27 |
| Arg | AGA | 1199.00 | 7.33 | 0.13 |
| Ser | AGT | 1170.00 | 7.15 | 0.10 |
| Ser | AGC | 2776.00 | 16.97 | 0.24 |
| Lys | AAG | 7241.00 | 44.25 | 0.79 |
| Lys | AAA | 1969.00 | 12.03 | 0.21 |
| Asn | AAT | 1946.00 | 11.89 | 0.33 |
| Asn | AAC | 3939.00 | 24.07 | 0.67 |
| Met | ATG | 4071.00 | 24.88 | 1.00 |
| Ile | ATA | 1014.00 | 6.20 | 0.13 |
| Ile | ATT | 2099.00 | 12.83 | 0.28 |
| Ile | ATC | 4403.00 | 26.91 | 0.59 |
| Thr | ACG | 1890.00 | 11.55 | 0.22 |
| Thr | ACA | 1620.00 | 9.90 | 0.19 |
| Thr | ACT | 1757.00 | 10.74 | 0.21 |
| Thr | ACC | 3236.00 | 19.78 | 0.38 |
| Trp | TGG | 1994.00 | 12.19 | 1.00 |
| End | TGA | 199.00 | 1.22 | 0.45 |
| Cys | TGT | 770.00 | 4.71 | 0.28 |
| Cys | TGC | 1963.00 | 12.00 | 0.72 |
| End | TAG | 121.00 | 0.74 | 0.28 |
| End | TAA | 120.00 | 0.73 | 0.27 |
| Tyr | TAT | 1303.00 | 7.96 | 0.27 |
| Tyr | TAC | 3440.00 | 21.02 | 0.73 |
| Leu | TTG | 1807.00 | 11.04 | 0.13 |
| Leu | TTA | 582.00 | 3.56 | 0.04 |
| Phe | TTT | 1697.00 | 10.37 | 0.29 |
| Phe | TTC | 4082.00 | 24.95 | 0.71 |
| Ser | TCG | 1620.00 | 9.90 | 0.14 |
| Ser | TCA | 1592.00 | 9.73 | 0.14 |
| Ser | TCT | 1792.00 | 10.95 | 0.15 |
| Ser | TCC | 2746.00 | 16.78 | 0.23 |
| Arg | CGG | 1505.00 | 9.20 | 0.16 |
| Arg | CGA | 610.00 | 3.73 | 0.06 |
| Arg | CGT | 1018.00 | 6.22 | 0.11 |
| Arg | CGC | 2562.00 | 15.66 | 0.27 |
| Gln | CAG | 4280.00 | 26.16 | 0.72 |
| Gln | CAA | 1626.00 | 9.94 | 0.28 |
| His | CAT | 1378.00 | 8.42 | 0.36 |
| His | CAC | 2431.00 | 14.86 | 0.64 |
| Leu | CTG | 4069.00 | 24.87 | 0.29 |
| Leu | CTA | 904.00 | 5.52 | 0.07 |
| Leu | CTT | 2415.00 | 14.76 | 0.17 |
| Leu | CTC | 4079.00 | 24.93 | 0.29 |
| Pro | CCG | 2642.00 | 16.15 | 0.29 |
| Pro | CCA | 2152.00 | 13.15 | 0.23 |
| Pro | CCT | 2102.00 | 12.85 | 0.23 |
| Pro | CCC | 2344.00 | 14.33 | 0.25 |
| *Saccharomyces cerevisiae* | | | | |
| Gly | GGG | 18129.00 | 6.18 | 0.12 |
| Gly | GGA | 32850.00 | 11.20 | 0.22 |
| Gly | GGT | 66575.00 | 22.69 | 0.45 |
| Gly | GGC | 28821.00 | 9.82 | 0.20 |
| Glu | GAG | 57100.00 | 19.46 | 0.30 |
| Glu | GAA | 133513.00 | 45.51 | 0.70 |
| Asp | GAT | 111120.00 | 37.88 | 0.65 |
| Asp | GAC | 58642.00 | 19.99 | 0.35 |
| Val | GTG | 32144.00 | 10.96 | 0.20 |
| Val | GTA | 35470.00 | 12.09 | 0.22 |
| Val | GTT | 63678.00 | 21.71 | 0.39 |
| Val | GTC | 33136.00 | 11.30 | 0.20 |
| Ala | GCG | 18402.00 | 6.27 | 0.11 |
| Ala | GCA | 47728.00 | 16.27 | 0.30 |
| Ala | GCT | 58916.00 | 20.08 | 0.37 |
| Ala | GCC | 35917.00 | 12.24 | 0.22 |
| Arg | AGG | 27990.00 | 9.54 | 0.21 |
| Arg | AGA | 61524.00 | 20.97 | 0.47 |
| Ser | AGT | 42499.00 | 14.49 | 0.16 |
| Ser | AGC | 29298.00 | 9.99 | 0.11 |
| Lys | AAG | 89539.00 | 30.52 | 0.42 |
| Lys | AAA | 124327.00 | 42.38 | 0.58 |
| Asn | AAT | 106379.00 | 36.26 | 0.60 |
| Asn | AAC | 71659.00 | 24.43 | 0.40 |
| Met | ATG | 61216.00 | 20.87 | 1.00 |
| Ile | ATA | 53773.00 | 18.33 | 0.28 |
| Ile | ATT | 88869.00 | 30.29 | 0.46 |
| Ile | ATC | 49422.00 | 16.85 | 0.26 |
| Thr | ACG | 24131.00 | 8.23 | 0.14 |
| Thr | ACA | 52363.00 | 17.85 | 0.31 |
| Thr | ACT | 58260.00 | 19.86 | 0.34 |
| Thr | ACC | 35998.00 | 12.27 | 0.21 |
| Trp | TGG | 30707.00 | 10.47 | 1.00 |
| End | TGA | 1901.00 | 0.65 | 0.30 |
| Cys | TGT | 23942.00 | 8.16 | 0.62 |
| Cys | TGC | 14448.00 | 4.93 | 0.38 |
| End | TAG | 1421.00 | 0.48 | 0.23 |
| End | TAA | 2985.00 | 1.02 | 0.47 |
| Tyr | TAT | 55441.00 | 18.90 | 0.57 |
| Tyr | TAC | 42016.00 | 14.32 | 0.43 |
| Leu | TTG | 79248.00 | 27.01 | 0.28 |

-continued

| AmAcid | Codon | Number | /1000 | Fraction |
|---|---|---|---|---|
| Leu | TTA | 77691.00 | 26.48 | 0.28 |
| Phe | TTT | 78451.00 | 26.74 | 0.59 |
| Phe | TTC | 53809.00 | 18.34 | 0.41 |
| Ser | TCG | 25856.00 | 8.81 | 0.10 |
| Ser | TCA | 55962.00 | 19.08 | 0.21 |
| Ser | TCT | 69019.00 | 23.53 | 0.26 |
| Ser | TCC | 41460.00 | 14.13 | 0.16 |
| Arg | CGG | 5414.00 | 1.85 | 0.04 |
| Arg | CGA | 9166.00 | 3.12 | 0.07 |
| Arg | CGT | 18429.00 | 6.28 | 0.14 |
| Arg | CGC | 7924.00 | 2.70 | 0.06 |
| Gln | CAG | 36018.00 | 12.28 | 0.31 |
| Gln | CAA | 78385.00 | 26.72 | 0.69 |
| His | CAT | 40211.00 | 13.71 | 0.64 |
| His | CAC | 22609.00 | 7.71 | 0.36 |
| Leu | CTG | 31503.00 | 10.74 | 0.11 |
| Leu | CTA | 39789.00 | 13.56 | 0.14 |
| Leu | CTT | 36697.00 | 12.51 | 0.13 |
| Leu | CTC | 16401.00 | 5.59 | 0.06 |
| Pro | CCG | 15796.00 | 5.38 | 0.12 |
| Pro | CCA | 51725.00 | 17.63 | 0.41 |
| Pro | CCT | 39402.00 | 13.43 | 0.31 |
| Pro | CCC | 20387.00 | 6.95 | 0.16 |

For each amino acid, the new pl-ole1 gene was designed the codon most preferred in Arabidopsis, with the following exceptions:

1. The codon for glutamine CAG was switched to CAA. Though the codon preference for glutamine is the same for both CAG and CAA in Arabidopsis, CAA was used since the AG motif is part of the 3' intron splice signal.

2. In OLE1, there are regions of high leucine/valine amino acid usage (e.g., between positions 322 to 571 of the nucleotide sequence are codons coding for 11 leucines and 7 valines). These regions correspond to the OLE1 protein transmembrane domains. If the most preferred codons in Arabidopsis (CTT and GTT, respectively) were used, the region would take on the characteristics of a plant intron, i.e., high T content, thereby introducing a number of highly probable 5' splice sites, which could not be removed without altering the amino acid sequence. Accordingly, a mixture of alternative codons was used for these amino acids. Similar changes were also applied to two other regions of OLE1 (positions 781 to 900 and positions 1081 to 1140).

Next, a search for problematic sequences, such as putative polyadenylation signals, hairpin cleavage consensus motifs, ATTTA motifs or concatamers thereof, was conducted. Such sequences are described in detail in U.S. Pat. No. 5,380,831 to Adang et al. (incorporated by reference herein). This search identified one hairpin cleavage consensus motif, CTTCGG, at position 553–559 of SEQ ID NO:1, which was removed by changing TTC to TTT (both encoding phenylalanine).

Next, a BamHI site and translation initiation consensus were added to the 5' end of the OLE1 coding sequence (M. Kozak, J. Biol. Chem. 266(30): 19867–19870, 1991). An XbaI and a BamHI site were added to the 3' end of the coding sequence. A PacI site was introduced into the same position as the original S. cerevisiae OLE1 PacI site (within the cytochrome $b_5$ domain), in order to provide a convenient restriction site for construction of this and other synthetic OLE1 genes. Other convenient restriction sites, which enable modular construction of synthetic OLE1 genes, are inherent within the final sequence of the new pl-ole1 gene.

Finally, the termination codon was checked against a stop codon consensus database, "TransTerm" (Dalphin et al., Nucl. Acids Res. 25(1): 246–247, 1997). The existing termination sequence, TGAT, appeared suitable for use in Arabidopsis, and so was not altered.

II. Construction of pl-ole1

The rebuilt pl-ole1 nucleotide sequence was constructed commercially (Operon Technologies, Inc.). The plasmid containing the rebuilt gene was designated pAMCM013. The pl-ole1 nucleotide sequence is set forth below as SEQ ID NO:3 (open reading frame starts at +11). This sequence encodes SEQ ID NO:2, but differs from the S. cerevisiae OLE1 gene (SEQ ID NO:1) in the following respects (summarized from above):

1. Arabidopsis thaliana codon usage; CAG switched to CAA for glutamine;

2. Translation initiation consensus added;

3. Hairpin removed;

4. Several (but not all) PlantNetGene predicted splice sites removed;

5. Eleven leucines changed from CTT to CTC, and 7 valines changed from GTT to GTG in positions 322–571, which corresponds to a plant intron-like region; similar changes made in regions 781–900 and 1081–1140; valine at position 432 retained as GTT to maintain Psp1406I site;

6. Certain leucine and valine codons were altered so that the same codons would not appear adjacent to others;

7. Intron acceptor site at position 1047 altered;

8. Restriction sites added to allow modular construction; PsP1406I site removed at position 1441; and 9. PacI site introduced at position 1362; an introduced NgoMI site at position 867 removed.

A gap alignment of SEQ ID NO: 1 (top) and SEQ ID NO: 3 (bottom) is shown below:

Gap alignment of wild type and rebuilt OLE1 sequences.
Percent Similarity: 79.871 Percent Identity: 79.871

```
  1 TACAACAAAGATGCCAACTTCTGGAACTACTATTGAATTGATTGACGACC    50
    |||   |||||  |||||||||||||||||||| ||  | ||  || || |
  1 ggatccaacaATGCCTACTTCTGGAACTACTATCGAGCTTATCGATGATC    50

51 AATTTCCAAAGGATGACTCTGCCAGCAGTGGCATTGTCGACGAAGTCGAC   100
    ||||  ||  |||||||||  |||||        ||| || || || || ||
 51 AATTCCCTAAGGATGATTCTGCTTCTTCTGGAATCGTTGATGAGGTTGAT   100

101 TTAACGGAAGCTAATATTTTGGCTACTGGTTTGAATAAGAAAGCACCAAG   150
    |  ||  || | ||||||  ||   ||||||||  |  ||  ||||||| || ||  ||
101 CTTACTGAGGCTAACATCCTTGCTACTGGACTTAACAAGAAGGCTCCTAG   150
```

-continued

```
151 AATTGTCAACGGTTTTGGTTCTTTAATGGGCTCCAAGGAAATGGTTTCCG 200
    ||| || |||||| || || ||| | |||||| || ||||| |||||||||| |
151 AATCGTTAACGGATTCGGATCTCTTATGGGATCTAAGGAGATGGTTTCTG 200

201 TGGAATTCGACAAGAAGGGAAACGAAAAGAAGTCCAATTTGGATCGTCTG 250
    | || |||||| |||||||||||||| ||||||||| || | ||| ||
201 TTGAGTTCGATAAGAAGGGAAACGAGAAGAAGTCTAACCTTGATAGACTT 250

251 CTAGAAAAGGACAACCAAGAAAAAGAAGAAGCTAAAACTAAAATTCACAT 300
    ||| || ||||| |||||||||| || || || ||||| ||||| || || ||
251 CTTGAGAAGGATAACCAAGAGAAGGAGGAGGCTAAGACTAAGATCCATAT 300

301 CTCCGAACAACCATGGACTTTGAATAACTGGCACCAACATTTGAACTGGT 350
    ||| || ||||| |||||| ||| ||||||||||| |||||| | |||||
301 CTCTGAGCAACCTTGGACTcTCAACAACTGGCATCAACATCTcAACTGGC 350

351 TGAACATGGTTCTTGTTTGTGGTATGCCAATGATTGGTTGGTACTTCGCT 400
    | |||||||| || || ||||| ||||| || || ||||||||| |||
351 TcAACATGGTgCTcGTcTGTGGAATGCCTATGATCGGATGGTACTTCGCT 400

401 CTCTCTGGTAAAGTACCTTTGCATTTAAACGTTTTCCTTTTCTCCGTTTT 450
    || ||||||||| || || |||||| | | |||||||||| ||||| || ||
401 CTcTCTGGAAAaGTgCCTCTcCATCTcAACGTTTTCCTcTTCTCTGTcTT 450

451 CTACTACGCTGTCGGTGGTGTTTCTATTACTGCCGGTTACCATAGATTAT 500
    |||||||||||| || || || ||||| ||||| || |||||||||| | |
451 CTACTACGCTGTTGGAGGAGTgTCTATCACTGCTGGATACCATAGACTcT 500

501 GGTCTCACAGATCTTACTCCGCTCACTGGCCATTGAGATTATTCTACGCT 550
    ||||||| |||||||||| ||||| ||||| | ||| | ||||||||||
501 GGTCTCATAGATCTTACTCTGCTCATTGGCCTCTTAGACTcTTCTACGCT 550

551 ATCTTCGGTTGTGCTTCCGTTGAAGGGTCCGCTAAATGGTGGGGCCACTC 600
    ||||| || ||||||||| ||||| || || ||||| |||||||| ||||
551 ATCTTtGGATGTGCTTCTGTTGAGGGATCTGCTAAGTGGTGGGGACATTC 600

601 TCACAGAATTCACCATCGTTACACTGATACCTTGAGAGATCCTTATGACG 650
    ||| |||||| || ||| | |||||||||||| | ||||||||||| ||||
601 TCATAGAATCCATCATAGATACACTGATACTCTTAGAGATCCTTACGATG 650

651 CTCGTAGAGGTCTATGGTACTCCCACATGGGATGGATGCTTTTGAAGCCA 700
    || | |||||| || |||||||| || |||||||||||||| | |||||
651 CTAGAAGAGGACTTTGGTACTCTCATATGGGATGGATGCTTCTTAAGCCT 700

701 AATCCAAAATACAAGGCTAGAGCTGATATTACCGATATGACTGATGATTG 750
    || || || |||||||||||||||||||||| || |||||||||||||||
701 AACCCTAAGTACAAGGCTAGAGCTGATATCACTGATATGACTGATGATTG 750

751 GACCATTAGATTCCAACACAGACACTACATCTTGTTGATGTTATTAACCG 800
    ||| || |||||||||||| ||||| |||||||||| | ||| | | ||| |
751 GACTATCAGATTCCAACATAGACATTACATCtTgCTcATGCTcCTTACTG 800

801 CTTTCGTCATTCCAACTCTTATCTGTGGTTACTTTTTCAACGACTATATG 850
    |||||||| || || ||||||| ||||| ||||||| || || |||
801 CTTTCGTgATCCCTACTCTcATCTGTGGATACTTCTTCAACGATTACATG 850

851 GGTGGTTTGATCTATGCCGGTTTTATTCGTGTCTTTGTCATTCAACAAGC 900
    || || | |||| | ||||| |||| |||||| |||| ||| ||||||||
851 GGAGGACTcATCTACGCTGGATTCATCAGAGTgTTCGTcATCCAACAAGC 900

901 TACCTTTTGCATTAACTCCATGGCTCATTACATCGGTACCCAACCATTCG 950
    ||| || || || ||||| ||||||||||||||||||| || ||||| ||||
901 TACTTTCTGTATCAACTCTATGGCTCATTACATCGGAACTCAACCTTTCG 950
```

```
                          -continued
 951 ATGACAGAAGAACCCCTCGTGACAACTGGATTACTGCCATTGTTACTTTC 1000
     ||||  ||||||||| |||   |  ||  ||||||||  |||||   ||  |||||||||||
 951 ATGATAGAAGAACTCCTAGAGATAACTGGATCACTGCTATCGTTACTTTC 1000

1001 GGTGAAGGTTACCATAACTTCCACCACGAATTCCCAACTGATTACAGAAA 1050
     || || ||  |||||||||||||| ||  ||  |||||  ||||||||||  |||||
1001 GGAGAGGGATACCATAACTTCCATCATGAGTTCCCTACTGATTAtAGaAA 1050

1051 CGCTATTAAGTGGTACCAATACGACCCAACTAAGGTTATCATCTATTTGA 1100
     ||||||| ||||||||||||||||  ||  |||||  ||  |||||||||  ||||
1051 CGCTATCAAGTGGTACCAATACGATCCTACTAAaGTgATCATCTACtTgA 1100

1101 CTTCTTTAGTTGGTCTAGCATACGACTTGAAGAAATTCTCTCAAAATGCT 1150
     |||||  |  ||  ||  || ||||| |    ||||||  |||||||||||||  |||
1101 CTTCTCTcGTgGGACTTGCTTACGATCTcAAGAAGTTCTCTCAAAACGCT 1150

1151 ATTGAAGAAGCCTTGATTCAACAAGAACAAAAGAAGATCAATAAAAAGAA 1200
     ||  || || ||  | ||  |||||||||  |||||||||||||||  ||  ||||||
1151 ATCGAGGAGGCTCTTATCCAACAAGAGCAAAAGAAGATCAACAAGAAGAA 1200

1201 GGCTAAGATTAACTGGGGTCCAGTTTTGACTGATTTGCCAATGTGGGACA 1250
     ||||||||||||||| |||||  ||  |||  |  ||||||| | || |||||||||  |
1201 GGCTAAGATtAAtTGGGGACCTGTTCTTACTGATCTTCCTATGTGGGATA 1250

1251 AACAAACCTTCTTGGCTAAGTCTAAGGAAAACAAGGGTTTGGTTATCATT 1300
     |  ||||| |||  | |||||||||||||||||| ||||||||| |  | ||||||||
1251 AGCAAACTTTCCTTGCTAAGTCTAAGGAGAACAAGGGACTTGTTATCATC 1300

1301 TCTGGTATTGTTCACGACGTATCTGGTTATATCTCTGAACATCCAGGTGG 1350
     |||||  ||  ||||||  ||  || ||||| || |||||||||  |||||   || ||
1301 TCTGGAATCGTTCATGATGTTTCTGGATACATCTCTGAGCATCCTGGAGG 1350

1351 TGAAACTTTAATTAAAACTGCATTAGGTAAGGACGCTACCAAGGCTTTCA 1400
     ||  |||||||||||  ||||||    |  ||  |||||  |||||  |||||||||
1351 AGAGACTtttaATtAAGACTGCTCTTGGAAAGGATGCTACTAAGGCTTTCT 1400

1401 GTGGTGGTGTCTACCGTCACTCAAATGCCGCTCAAAATGTCTTGGCTGAT 1450
     |||  || ||  |||  || || || ||  |||||||||||  |  ||||||
1401 CTGGAGGAGTTTACAGACATTCTAACGCTGCTCAAAACGTGCTTGCTGAT 1450

1451 ATGAGAGTGGCTGTTATCAAGGAAAGTAAGAACTCTGCTATTAGAATGGC 1500
     ||||||||  |||||||||||||    |||||||||||||  ||||||||
1451 ATGAGAGTTGCTGTTATCAAGGAGTCTAAGAACTCTGCTATCAGAATGGC 1500

1501 TAGTAAGAGAGGTGAAATCTACGAAACTGGTAAGTTCTTTTAAGCATCAC 1550
     |   |||||||||  || ||||||||  |||||  ||||||||| | | |  |
1501 TTCTAAGAGAGGAGAGATCTACGAGACTGGAAAGTTCTTCTGAtctagag 1550

1551 ATTAC                                             1555
     | |
1551 gatcc                                             1555
```

The pl-ole1 synthetic gene contains no intron-like regions, or predicted splice sites within its sequence. Moreover, comparing the codon usage of Arabidopsis with that of *Brassica napus, Phaseolus vulgaris* or *Zea mays*, with the exception of cystein (a rare amino acid that comprises 1.7% of all Arabidopsis codons, and occurs 4 times (0.8%) in OLE1), the sequence contains no rare codons for any of those species. The codon usage of pl-ole1 is particularly similar to the preferred usage of *Brassica napus*. Accordingly, pl-ole1 is expected to be particularly well expressed in all those species, and well expressed in any plant species.

An alternative version of pl-ole1, referred to herein as pl-ole1-2, was also constructed. This synthetic gene was modified only in specific codons identified as high frequency splicing signals. It was discovered that this construct is expressed equally as well as pl-ole1 in Arabidopsis.

EXAMPLE 2

Vacuum Infiltration Transformation of *Arabidopsis thaliana* with pl-ole1

A modification of a transformation protocol of Pam Green (http://www.bch.msu.edu/pamgreen/vac.html) was used for the transformation of *A. thaliana* with pl-ole1. The protocol was adapted from protocols by Nicole Bechtold and Andrew Bent. This protocol gives very good results, with 95% of all infiltrated plants giving rise to transformants, and a transformant in up to 1 in 25 seeds.

Protocol

1. Seeds of *Arabidopsis thaliana* ecotype Columbia were sown in lightweight plastic pots prepared in the following way: mound Arabidopsis soil mixture into 3 to 4 inch pots, saturate soil with Arabidopsis fertilizer, add more soil so that it is rounded about 0.5 above the edge.

2. Plants were grown under conditions of 16 hours light/8 hours dark at 20° C., fertilizing with Arabidopsis fertilizer once a week from below, adding about 0.5 L to each flat. After 4–6 weeks, plants were considered ready for vacuum infiltration when primary inflorescence was 10–15 cm tall and the secondary inflorescences appeared at the rosette. The bolts were clipped back and 2 to 3 days was allowed for them to regrow before infiltration.

3. in the meantime, the construct was transformed into *Agrobacterium tumefaciens* strain (LBA4404). When plants were ready to transform, a 50 mL culture of LB medium containing 50 mg/L kanamycin and 50 mg/L of streptomycin was inoculated with a 1 mL overnight starter culture.

4. Cultures were grown overnight at 28° C. with shaking. The culture was pelleted, the supernatant removed, and the pellet resuspended in 250 ml of infiltration medium to OD600>0.8. Infiltration medium (1 liter) comprised 2.2 g MS salts, 1×B5 vitamins, 50 g sucrose, 0.5 g MES, pH to 5.7 with KOH, 0.044=B5M benzylaminopurine, 200=B5L Silwet L-77 (OSI Specialties).

5. The resuspended culture was placed in a magenta jar inside a large bell jar. Pots containing plants to be infiltrated were inverted into the solution so that the entire plant was covered, including rosette, but none of the soil was submerged.

6. A vacuum of 400 mm Hg (about 17 inches) was drawn. Once the vacuum level was reached, the suction was closed and the plants allowed to remain under vacuum for five minutes. The vacuum was then quickly released. The pots were briefly drained, then placed on their sides in a tray, which was covered with a humidome to maintain humidity. The next day, the plants were removed to the growth room, the pots uncovered and set upright. Plants infiltrated with different constructs were kept separated in different trays thereafter.

7. Plants were allowed to grow under the same conditions as before. Plants were staked individually as the bolts grew. When plants were finished flowering, water was gradually reduced, then eliminated to allow the plants to dry out. Seeds were harvested from each plant individually.

8. Large selection plates were prepared: 4.3 g/L MS salts; 1×E5 vitamins (optional); 1% sucrose; 0.5 g/L MES pH to 5.7 with KOH; 0.8% phytagar—Autoclaved, then added antibiotics (35 µg/mL kanamycin and 250 µg/mL of carbenicillin) and 150×15 mm plates were poured.

9. Plates were dried well in the sterile hood before plating—20–30 minutes with the lids open was usually sufficient.

10. For each plant, up to 100 µL of seeds (approximately 2500 seeds) was sterilized and plated out individually. Seeds were sterilized as follows: 1 min in 70% ethanol, 7 minutes in 50% bleach/0.02% Triton X-100 with vortexing, 6 rinses in sterile distilled water. Seeds were resuspended in 2 mL sterile 0.1% agarose and poured onto large selection plates as if plating phage. Plates were tilted so seeds were evenly distributed, and allowed to sit 10–15 minutes, during which time the liquid soaked into the medium. Plates were sealed with Parafilm and placed in a growth room.

11. After 7 to 10 days, transformants were visible as dark green plants. These were transferred onto "hard selection" plates (100×15 mm plates with same recipe as selection plates but with 1.5% phytagar) to eliminate any pseudo-resistants, then replaced in the growth room.

12. After 10 to 14 days, the plants possessed at least two sets of true leaves. At this point, plants were transferred to soil, covered with plastic, and moved to a growth chamber with normal conditions. They were typically kept covered for several days.

References

Bechtold N, Ellis J, Pelletier G (1998) Methods Mol Biol. 82: 259–266.

Bent A, Kunkel B N, Dahlbeck D, Brown K L, Schmidt R, Giraudat J, Leung J, Staskawicz B J (1994) Science 265: 1856–1860.

Koncz C, Schell J (1986) Mol. Gen. Genet. 204: 383–396.

Solutions

1000×B5 Vitamins (10 mL)
   1000 mg myo-inositol
   100 mg thiamine-HCl
   10 mg nicotinic acid
   10 mg pyridoxine-HCl
   Dissolve in ddH2O and store at −20° C.

Arabidopsis Fertilizer (10 liters)
   50 mL 1M KNO3
   25 mL 1M KPO4 (pH 5.5)
   20 mL 1M MgSO4
   20 mL 1M Ca(NO3)2
   5 mL 0.1M Fe.EDTA
   10 mL micronutrients (see below)
   Dissolve in ddH2O and store at room temperature Arabidopsis Micronutrients (500 mL)
   70 mL 0.5M boric acid
   14 mL 0.5M MnCl2
   2.5 mL 1M CuSO4
   1 mL 0.5M ZnSO4
   1 mL 0.1M NaMoO4
   1 mL 5M NaCl
   0.05 mL 0.1M CuCl2
   Dissolve in ddH2O and store at room temperature

EXAMPLE 3

Customizing OLE1 to Express Post-Translational Modifications

After determining the optimized codon preferences of OLE1 mRNA (or mRNA derived from another fungal or animal desaturase) for high level expression in the host plant, specific amino acids that are involved in the post-translational control of enzyme activity or stability are altered to maximize the catalytic activity of the expressed enzyme. There are a number of protein kinase and/or phosphorylase consensus sequences that are highly conserved in the fungal and animal desaturases. These are shown below. First is shown a table of aligned potential phosphorylation sites in desaturases. Next is shown a pileup of Δ-9 fatty acid desaturases. PROSITE analysis of these desaturases predicts a number of potential phosphorylation sites, highlighted by bold underlined characters.

TABLE 2

Aligned Potential phosphorylation sites in desaturases.
Phosphorylation sites are indicated with respect to amino acid
positions in the Olelp protein coding sequence.
Abbreviations, S = serine, T = Threonine, A = Alanine,
PKC — protein kinase C like; CK-2 — casein kinase II like;
CAMP — cAMP activated kinase (PKA) like;
np., not predicted as a phosphorylation site.

| Residue position | Olelp Residue | Olelp sequence | Phosphorylation type | Fungal/b5 | Animal | Insect |
|---|---|---|---|---|---|---|
| 166 | S | SHR | PKC | mixed, S or A | all S, SHR | N.P., A |
| 169 | T | np | PKC | S or A | all TYK or SYK | SYK |
| 191 | S | SAK | PKC | all S | all D | all A |
| 206 | T | np | CK-2 | all T | all S | all S |
| 208 | T | TLRD | CK-2 | all T | all T | all T |
| 215 | A | np | PKC | A or V | all S | all A |
| 323 | T | TPRD | CK-2 | T or S | S or np | np |
| 351 | R | np | CK-2 | all R | all S | all K |
| 383 | S | KKFS | CAMP | S or np | all S | all S but np |

Pileup of Δ-9 fatty acid desaturases showing potential phosphorylation sites

```
                   1                                                    50
           Rat     ~~~~~~~~~~ ~~~~~~~~~~ ~~~~~~~~~~ ~~~~~~MPAHM LQE.ISSSY.
         Mouse     ~~~~~~~~~~ ~~~~~~~~~~ ~~~~~~~~~~ ~~~~~~MPAHM LQE.ISSSY.
         Sheep     ~~~~~~~~~~ ~~~~~~~~~~ ~~~~~~~~~~ ~~~~~~MPAHL LQEEISSSY.
           Pig     ~~~~~~~~~~ ~~~~~~~~~~ ~~~~~~~~~~ ~~~~~~~~~~ ~~~~~~SSY.
         Human     ~~~~~~~~~~ ~~~~~~~~~~ ~~~~~~~~~~ ~~~~~~MPAHL LQDDISSSY.
       Hamster     ~~~~~~~~~~ ~~~~~~~~~~ ~~~~~~~~~~ ~~~~~~MPGHL LQEEMTSSYT
    Drosophila     ~~~~~~~~~~ ~~~~~~~~~~ ~~~~~~~~~~ ~~~~~~~MPP NAQAGAQSIS
          Moth     ~~~~~~~~~~ ~~~~~~~~~~ ~~~~~~~~~~ ~~~~~~~~~~ ~~~~~~~~~~
     C. elegans    ~~~~~~~~~~ ~~~~~~~~~~ ~~~~~~~~~~ ~~MTVKTRSN IAKKIEKDGG
  S. cerevisiae    MPTSGTTIEL IDDQFPKDDS ASSGIVDEVD LTEANILATG LNKKAPRIVN
      P. angusta   ~~~~~~~~~~ ~~~~~~~~~~ ~~~~~~~~~~ ~~~~~~~~~~ ~~~~~~~~~~
   H. capsulatum   ~~~~~~~~~~ ~~~~~~~~~~ ~~~~~~~~~~ ~~~~~~~~~~ ~~~~~~~~~~
       M. rouxii   ~~~~~~~~~~ ~~~~~~~~~~ ~~~~~~~~~~ ~~~~~~~~~~ ~~~~~~~~~~
     C. curvatus   ~~~~~~~~~~ ~~~~~~~~~~ ~~~~~~~~~~ ~~~~~~~~~~ ~~~~~~~~~~
      C. merolae   ~~~~~~~~~~ ~~~~~~~~~~ ~~~~~~~~~~~MTAKVESKVR EEEKGSNPST 51                                                   100
           Rat     TTTTTITEPP SGNLQNGREK MKKVPLYLEE DI.....RPE MREDIHDPSY
         Mouse     TTTTTITAPP SG...NEREK VKTVPLHLEE DI.....RPE MKEDIHDPTY
         Sheep     TTTTTITAPP SRVLQNGGGK LEKTPLYLEE DI.....RPE MRDDIYDPNY
           Pig     TTTTTITAPS SRVLQNGGGK SEKTPQYVEE DI.....RPE MKDDIYDPTY
         Human     TTTTTITAPP PGVLQNGGDK LETMPLYLED DI.....RPD IKDDIYDPTY
       Hamster     TTTTTITEPP SESLQ..... .KTVPLYLEE DI.....RPE MKEDIYDPSY
    Drosophila     DSLIAAASAA ADAGQSPTKL QEDSTGVLFE CD.....VET TDGGLVKDTT
          Moth     ~~~~~~~~~~ ~~~~~MPPQG QTGGSWVLYE TD.....AVN TDTD..APVI
     C. elegans    PETQYLAVDP NEIIQLQEES KKVVPKCLPA RLPTAACKAS QENGECQKTV
  S. cerevisiae    GFGSLMGSKE MVSVEFDKKG NEKKSNLDRL LEKDNQEKEE AKTKIH.ISE
      P. angusta   ~~~~~~~~~~MGTKS MTDVTAEEL. ..SKDSVAMM LAKDRELKNK YLKQKH.ISE
   H. capsulatum   ~~~~~~~~MA LNEAPTASPV AETAAGGKDV VTDAARRPNS EPKKVH.ITD
       M. rouxii   ~~~~~~~~~~ ~~~~~~~MSN IATLTGSTART KTESMKPPLP KTKMPP.LFD
     C. curvatus   ~MSASTKQAS TTVAQPSGKP VTNVIDPERD DFIVPDNYVT RTVENM.KML
      C. merolae   AAADDSGAVI PTLKPRPKPA VEPLEREGVE FDPQRGLVFE KTRSSKWMSE 101                                                   150
           Rat     QDEEGPPPKL EYVWRNIILM ALLHVGALYG ITL.IPSSKV YTLLWGIFYY
         Mouse     QDEEGPPPKL EYVWRNIILM VLLHLGGLYG IIL.VPSCKL YTALFGIFYY
         Sheep     QDKEGPKPKL EYVWRNIILM GLLHLGALYG ITL.IPTCKI YTFLWVLFYY
           Pig     QDKEGPQGKL EYVWRNIILM SLLHLGALYG IIL.IPTCKI YTLLWAFAYY
         Human     QDKEGPSPKV EYVWRNIILM SLLHLGALYG ITL.IPTCKF YTWLWGVFYY
       Hamster     QDEEGPPPKL EYVWRNIILM ALLHLGALYG LVL.VPSSKV YTLLWAFVYY
    Drosophila     VMKKAEKRLL KLVWRNIIAF GYLHLAALYG AYLMVTSAKW QTCILAYFLY
          Moth     VPPSAEKREW KIVWRNVILM GMLHIGGVYG AYLFLTKAMW LTDLFAFFLY
     C. elegans    FLEIVIPYKM EIVWRNVALF AALHFAAAIG LYQLIFEAKW QTVIFTFLLY
  S. cerevisiae    QPWTLNNWHQ HLNWLNMVLV CGMPMIGWYF ALSGKVPLHL NVFLFSVFYY
      P. angusta   QPWTWENWHR HINWLNFILV LAVPFAG..L ISTKWVPLKL HTFVTAVILY
   H. capsulatum   TPITLANWHK HISWLNVTLT IAIPIYG..L VQAYWVPLHL KTALWAVVYY
       M. rouxii   QPVTSKNWTK FVNWPQAILL CVTPLIALYG IFT..TELTK KTLIWSWIYY
     C. curvatus   PPVTWRNLHK NIQWISFLAL TIPPAMAIYG LCT..VPVQT KTFIWSVVYY
      C. merolae   KELNELPLLQ RINWLS.TSI IFTPLIGT.L IGIWFVPLQR KTLVLAIVTY
```

-continued

```
                     151                                                         200
           Rat  LISALGITAG AHRLWSHRTY KARLPLRIFL IIANTMAFQN DVYEWARDHR
         Mouse  MTSALGITAG AHRLWSHRTY KARLPLRIFL IIANTMAFQN DVYEWARDHR
         Sheep  VISALGITAG VHRLWSHRTY KARLPLRVFL IIANTMAFQN DVFEWSRDHR
           Pig  LLSAVGVTAG AHRLWSHRTY KARLPLRVFL IIANTMAFQN DVYEWARDHR
         Human  FVSALGITAG AHRLWSHRSY KARLPLRLFL IIANTMAFQN DVYEWARDHR
       Hamster  VISIEGIGAG VHRLWSHRTY KARLPLRIFL IIANTMAFQN DVYEWARDHR
    Drosophila  VISGLGITAG AHRLWAHRSY KAKWPLRVIL VIFNTIAFQD AAYHWARDHR
          Moth  LCSGLGITAG AHRLWAHKSY KARLPLRLLL TLFNTLAFQD AVIDWARDHR
     C. elegans VFGGFGITAG AHRLWSHKSY KATTPMRIFL MILNNIALQN DVIEWARDHR
  S. cerevisiae AVGGVSITAG YHRLWSHRSY SAHWPLRLFY AIFGCASVEG SAKWWGHSHR
     P. angusta CFGGISITAG YHRHWAHRAY DCKLPVKIFF ALFGASAVEG SIKMWGHQHR
   H. capsulatum FMTGLGITAG YHRLWAHCSY SATLPLKIYL AAVGGGAVEG SIRWWARGHR
      M. rouxii FITGLGITAG YHRMWSHRAY RGTDLLRWFM SFAGAGAVEG SIYWWSRGHR
     C. curvatus FITGLGITAG YHRLWAHRSY NASKPLQYFL ALCGAGSVQG SIRWWSRGHR
      C. merolae FCCGLGITGG YHRLWSHRSY EAHWLVQVIL ACFGAAAFEG SARYWCRLHR 201                                                         250
           Rat  AHHKFSETHA DPHNSRRGFF FSHVGWLLVR KHPAVKEKGG KLDMSDLKAE
         Mouse  AHHKFSETHA DPHNSRRGFF FSHVGWLLVR KHPAVKEKGG KLDMSDLKAE
         Sheep  AHHKFSETDA DPHNSRRGFF FSHVGWLLVR KHPAVREKGA TLDLSDLRAE
           Pig  AHHKFSETDA DPHNSRRGFF FSHVGWLLVR KHPAVKEKGG LLNMSDLKAE
         Human  AHHKFSETHA DPHNSRRGFF FSHVGWLLVR KHPAVKEKGS TLDLSDLEAE
       Hamster  AHHKFSETYA DPHNSRRGFF FSHVGWLLVR KHPAVKEKGG KLDMSDLKAE
    Drosophila  VHHKYSETDA DPHNATRGFF FSHVGWLLCK KHPEVKAKGK GVDLSDLRAD
          Moth  MHHKYSETDA DPHNATRGFF FSHVGWLLVR KHPQIKAKGH TIDLSDLKSD
    C. elegans  CHHKWTDTDA DPHNTTRGFF FAHMGWLLVR KHPQVKEQGA KLDMSDLLSD
  S. cerevisiae IHHRYTDTLR DPYDARRGLW YSHMGWMLLK PNP...KYKA RADITDMTDD
     P. angusta VHHRYTDTPR DPYDAKRGFW YSHMGWMLLV PNP...RYKA RADISDLLDD
  H. capsulatum AHHRYTDTDK DPYSVRKGLL YSHIGWMVMK QNP...KRIG RTEITDLNED
      M. rouxii AHHRWTDTDK DPYSAHRGFF FSHFGWMLVQ RPK...NRIG YADVADLKAD
    C. curvatus AHHRYTDTKL DPYSAHEGFW HAHMGWMLI. KPR...GKIG VADISDLSKN
     C. merolae AHHRYVDSDR DPYAVEKGFW YAHLWWMVFK LPR...QRQG RVDITDLNAN 251                                                         300
           Rat  KLVMFQRRYY KPGLLLMCFI LPTLVPWYCW GETFLHSLFV STFLRYTLVL
         Mouse  KLVMFQRRYY KPGLLLMCFI LPTLVPWYCW GETFVNSLFV STFLRYTLVL
         Sheep  KLVMFQRRYY KPGVLLLCFI LPTLVPWYLW GESFQNSLFF ATFLRYAVVL
           Pig  KLVMFQRRYY KPGILLMCFI LPTIVPWYCW GEAFPQSLFV ATFLRYAIVL
         Human  KLVMFQRRYY KPGLLMMCFI LPTLVPWYFW GETFQNSVFV ATFLRYAVVL
       Hamster  KLVMFQRRYY KPAILLMCFI LPTFVPWYFW GEAFVNSLCV STFLRYALVL
    Drosophila  PILMFQKKYY MILMPIACFI IPTVVPMYAW GESFMNAWFV ATMFRWCFIL
          Moth  PILRFQKKYY LTLMPLICFI LPSYIPT.LW GESAFNAFFV CSIFRYVYVL
    C. elegans  PVLVFQRKHY FPLVILCCFI LPTIIPVYFW KETAFIAFYT AGTFRYCFTL
  S. cerevisiae WTIRFQHRHY ILLMLLTAFV IPTLICGYFI ND.YMGGLIY AGFIRVFVIQ
     P. angusta WVVRVQHRHY LLLMVVMAFL FPAVLTHYLF ND.FWGGFIY AGLLRAVVIQ
  H. capsulatum PVVVWQHRNY LKVVIFMGIV FPMLVSGLGW GD.WFGGFIY AGILRIFFVQ
      M. rouxii HVVAFQHKYY PYFALGMGFI FPTLVAGLGW GD.FRGGYFY AGVLRLCFVH
    C. curvatus PVVKWQHNNY VALLFFMGLA FPTLVAGLGW GD.WWGGLFF AGAARLVFVH
     C. merolae PILRFQHRYY LQIAILFSFV IPLTISTLGW GD.FWGGLVY ACLGRMLFVQ 301                                                         350
           Rat  NATWLVNSAA HLYGYRPYDK NIQSRENILV SLGSVGEGFH NYHHAFPYDY
         Mouse  NATWLVNSAA HLYGYRPYDK NIQSRENILV SLGAVGEGFH NYHHTFPYDY
         Sheep  NATWLVNSAA HMYGYRPYDK TINPRENILV SLGAVGEGFH NYHHTFPYDY
           Pig  NATWLVNSAA HLYGYRPYDK TISPRENILV SLGAVGEGFH NYHHTFPYDY
         Human  NATWLVNSAA HLFGYRPYDK NISPRENILV SLGAVGEGFH NYHHSFPYDY
       Hamster  NATWLVNSAA HLYGYRPYDK NIDPRENALV SLGCLGEGFH NYHHAFPYDY
    Drosophila  NVTWLVNSAA HKFGGRPYDK FINPSENISV AILAFGEGWH NYHHVFPWDY
          Moth  NVTWLVNSAA HLWGSKPYDK NINPVETRPV SLVVLGEGFH NYHHTFPWDY
    C. elegans  HATWCINSAA HYFGWKPYDS SITPVENVFT TIAAVGEGGH NFHHTFPQDY
  S. cerevisiae QATFCINSLA HYIGTQPFDD RRTPRDNWIT AIVTFGEGYH NFHHEFPTDY
     P. angusta QATFCVNSLA HWIGEQPFDD RRTPRDHVLT ALVTFGEGYH NFHHEFPSDY
  H. capsulatum QATFCVNSLA HWLGDQPFDD RNSPRDHIVT ALVTLGEGYH NFHHEFPSDY
      M. rouxii HATFCVNSLA HYLGESTFDD HNTPRDSWVT ALVTMGEGYH NFHHFPQDY
    C. curvatus HSTFCVNSLA HWLGETPFDN KHTPKDHFIT ALVTVGEGYH NFHHQFPMDF
     C. merolae QSTFCVNSLA HWWGEQTFSR RHTSYDSVIT ALVTLGEGYH NFHHEFPHDY 351                                                         400
           Rat  SASEY.RWHI NFTTFFIDCM AALGLAYDRK KVSKAAVLAR IKRTGDGSHK
         Mouse  SASEY.RWHI NFTTTFIDCM AALGLAYDRK KVSKATVLAR IKRTGDGSHK
         Sheep  SASEY.RWHI NFTTTFIDCM AAIGLAYDRK KVSKAAVLGR MKRTGEESYK
           Pig  SASEY.RWHI NLTTFFIDCM AALGLAYDRK KVSKAAIL~~ ~~~~~~~~~~
         Human  SASEY.RWHI NFNTFFIDWM AALGLTAYDRK KVSKAAILAR IKRTGDGNYK
       Hamster  SASEY.RWHI NFTTTFIDCM AALGLAYDRK KVSKAAVLAR IKRTGDGSCK
    Drosophila  KTAEFGKYSL NFTTAFIDFF AKIGWAYDLK TVSTDIIKKR VKRTGDGTHA
          Moth  KTAELGDYSL NFTKMFIDFM ASIGWAYDLK TVSTDVIQKR VKRTGDGSHA
    C. elegans  RTSEYS.LKY NWTRVLIDTA AALGLVYDRK TACDEIIGRQ VSNHGCDIQR
  S. cerevisiae RNA.IKWYQY DPTKVIIYLT SLVGLAYDLK KFSQNAIEEA LIQQEQKKIN
```

```
            -continued
   P. angusta   RNA.LKWYQY DPTKVVIYLL SKVGLAYNLK KFSQNAIDQG ILQQQQKKLD
H. capsulatum   RNA.IEWHQY DPTKWTIWIW KQLGLAYDLK QFRANEIEKG RVQQLQKKID
    M. rouxii   RNA.IKFGQY DPTKWKIIVL SWFGLAYELK QFPTNEVTKG RLFMEEKRIQ
   C. curvatus  RNA.IKWYQY DPTKWFIWTM AQLGLASHLK KFPDNEIKKG QYTMKLMQLQ
   C. merolae   RNG.VVWYHW DPTKWVIRLL SWAGLAWHLV RFPRNELVKA RLQVRQEILD 401                                                450
          Rat   SS*~~~~~~~ ~~~~~~~~~~ ~~~~~~~~~~ ~~~~~~~~~~ ~~~~~~~~~~
        Mouse   SS~~~~~~~~ ~~~~~~~~~~ ~~~~~~~~~~ ~~~~~~~~~~ ~~~~~~~~~~
        Sheep   SG~~~~~~~~ ~~~~~~~~~~ ~~~~~~~~~~ ~~~~~~~~~~ ~~~~~~~~~~
          Pig   ~~~~~~~~~~ ~~~~~~~~~~ ~~~~~~~~~~ ~~~~~~~~~~ ~~~~~~~~~~
        Human   SG~~~~~~~~ ~~~~~~~~~~ ~~~~~~~~~~ ~~~~~~~~~~ ~~~~~~~~~~
      Hamster   SG~~~~~~~~ ~~~~~~~~~~ ~~~~~~~~~~ ~~~~~~~~~~ ~~~~~~~~~~
   Drosophila   TWGWGDVDQP KEEIE.DAVI THKKSE~~~~ ~~~~~~~~~~ ~~~~~~~~~~
         Moth   VWGWDDHEVH QEDKKLAAII NPEKTE~~~~ ~~~~~~~~~~ ~~~~~~~~~~
    C. elegans  GKSIM~~~~~ ~~~~~~~~~~ ~~~~~~~~~~ ~~~~~~~~~~ ~~~~~~~~~~
 S. cerevisiae  KKKAKINWGP VLTDLPMWDK QTFLAKS.KE NKGLVIISGI VHDVSGYISE
    P. angusta  RMRAKLNWGP QLSELPVWDK STFFEKA.KE QKGLVIISGI VHDCANFLTE
 H. capsulatum  QRRAKLDWGI PLEQLPVIEW DDYVDQA.KN GRGLIAIAGV VHDVTDFIKD
     M. rouxii  AQKAKLSYGT PLKDLPIYTW EEYQSLVLND NKKWVLIEGV LYDVEEFMKE
   C. curvatus  EQSEKLEWPK HSNDLPVISW EDFQA..ESK TRALIAVHGF IHDCSSFIED
    C. merolae  EAKKRVDWGK PIESLPVTTW KDVQRLAKEE NRLLVVIEGI VHDCTRFKVQ 451                                                500
          Rat   ~~~~~~~~~~ ~~~~~~~~~~ ~~~~~~~~~~ ~~~~~~~~~~ ~~~~~~~~~~
        Mouse   ~~~~~~~~~~ ~~~~~~~~~~ ~~~~~~~~~~ ~~~~~~~~~~ ~~~~~~~~~~
        Sheep   ~~~~~~~~~~ ~~~~~~~~~~ ~~~~~~~~~~ ~~~~~~~~~~ ~~~~~~~~~~
          Pig   ~~~~~~~~~~ ~~~~~~~~~~ ~~~~~~~~~~ ~~~~~~~~~~ ~~~~~~~~~~
        Human   ~~~~~~~~~~ ~~~~~~~~~~ ~~~~~~~~~~ ~~~~~~~~~~ ~~~~~~~~~~
      Hamster   ~~~~~~~~~~ ~~~~~~~~~~ ~~~~~~~~~~ ~~~~~~~~~~ ~~~~~~~~~~
   Drosophila   ~~~~~~~~~~ ~~~~~~~~~~ ~~~~~~~~~~ ~~~~~~~~~~ ~~~~~~~~~~
         Moth   ~~~~~~~~~~ ~~~~~~~~~~ ~~~~~~~~~~ ~~~~~~~~~~ ~~~~~~~~~~
   C. elegans   ~~~~~~~~~~ ~~~~~~~~~~ ~~~~~~~~~~ ~~~~~~~~~~ ~~~~~~~~~~
 S. cerevisiae  HPGGETLIKT ALGKDATKAF SGGVYRHSNA AQNVLADMRV AVIKESKNSA
    P. angusta  HPGGQALLKT SFGKDATMAF NGGVYAHSNA AHNLLATMRV AVIRDGGANG
 H. capsulatum  HPGGKAMINS GIGKDATAMF NGGVYNHSNA AHNQLSTMRV GVIRGGCEVE
     M. rouxii  HPGGMKYLST AVGKDMTTAF NGGIYNHSNG TRNLLTSLRV GVLRNGMQV.
   C. curvatus  HPGGAHLIKR AIGTDSTTAF FGGVYDHSNA AHNLLAMMRV GVLDGGMEVE
    C. merolae  HPGGQRILEF WNVRDATQAF NGDVYNHTKA ARNLLAHLRV AQLKEIYEPE
```

Protein kinase (specifically cAMP- and cGMP-dependent) phosphorylation sites.

There have been a number of studies relative to the specificity of cAMP- and cGMP-dependent protein kinases (Fremisco J. R. et al., J. Biol. Chem. 255:4240–4245, 1980; Glass D. B., Smith S. B., J. Biol. Chem. 258:14797–14803, 1983; Glass D. B. et al., J. Biol. Chem. 261:2987–2993, 1986). Both types of kinases appear to share a preference for the phosphorylation of serine or threonine residues found close to at least two consecutive N-terminal basic residues. It is important to note that there are quite a number of exceptions to this rule. However, the consensus pattern is as follows: [RK] (2)-x-[ST], where S or T is the phosphorylation site.

Protein kinase C phosphorylation site.

In vivo, protein kinase C exhibits a preference for the phosphorylation of serine or threonine residues found close to a C-terminal basic residue (Woodget J. R. et al., Eur. J. Biochem. 161:177–184, 1986;. Kishimoto A. et al., J. Biol. Chem. 260:12492–12499, 1985). The presence of additional basic residues at the N- or C-terminus of the target amino acid enhances the Vmax and Km of the phosphorylation reaction. The consensus pattern is: [ST]-x-[RK] where S or T is the phosphorylation site.

Casein kinase II phosphorylation site.

Casein kinase II (CK-2) is a protein serine/threonine kinase whose activity is independent of cyclic nucleotides and calcium. CK-2 phosphorylates many different proteins. The substrate specificity (Pinna L. A., Biochim. Biophys. Acta 1054:267–284, 1990) of this enzyme can be summarized as follows: (1) Under comparable conditions Ser is favored over Thr; (2) an acidic residue (either Asp or Glu) must be present three residues from the C-terminal end of the phosphate acceptor site; (3) additional acidic residues in positions +1, +2, +4, and +5 increase the phosphorylation rate (most physiological substrates have at least one acidic residue in these positions); (4) Asp is preferred to Glu as the provider of acidic determinants; and (5) a basic residue at the N-terminus of the acceptor site decreases the phosphorylation rate, while an acidic one will increase it. The consensus pattern is: [ST]-x(2)-[DE] where S or T is the phosphorylation site (note: this pattern is found in most of the known physiological substrates).

If phosphorylation of a specific site by any kinase is found to increase the catalytic activity or stability of the encoded desaturase protein, the phosphorylated serine or threonine residue is changed to encode a negatively charged amino acid (aspartic acid or glutamic acid) in order to permanently optimize the activity or the protein. If phosphorylation of a specific residue is found to decrease the activity or stability of the encoded desaturase, the affected serine or threonine encoding codon is altered to substitute a neutral or a positively charged amino acid that will permanently optimize the activity or stability of the protein.

EXAMPLE 4

Further Modifications and Improvements of the *Saccharomyces cerevisiae* OLE1 Gene for Plant Expression Using Elements Derived from Native Plant Desaturase Genes The activity of the native or modified forms of the *Saccharoznyces cerevisiae* OLE1 Δ-9 desaturase gene in plant tissues may be further improved by the substitution or inclusion of elements derived from native plant desaturase genes. Favorable plant gene elements may include sequences that improve the expression of the modified gene at one or more levels, including the following: 1) transcription, 2) pre-mRNA processing, 3) mRNA transport from the nucleus to the cytoplasm, 4) mRNA stability 5) translation, 6) targeting or retention of the protein at the appropriate membrane surface or organelle surface, 7) protein folding and maturation, and 8) stability of the functional desaturase protein.

The inventors have shown that the OLE1 gene can tolerate significant modifications without losing its biological activity. These modifications include deletion of the "coiled coil" region, the addition of 239 amino acids to the N-terminus of OLE1p and truncation of 55 and 60 amino acids from the N-terminal end of the protein. The inventors have also shown that modifications of the 5' and 3' untranslated regions of the OLE1 mRNA can significantly affect its stability. For example, removing a short open reading frame near the 5' "cap" region of the OLE1 mRNA increases its half-life in Saccharomyces from 12 minutes to approximately 25 minutes. The existence of elements in the mRNA that affect its stability indicate that other elements might also exist that affect the stability of an mRNA generated by a synthetic gene in another host organism.

Plant desaturase gene elements that enhance the function of the modified Δ-9 desaturase gene are identified by a 2-step method. STEP 1 involves isolating a series of DNA sequences from a cDNA that encodes a plant ER lipid biosynthetic enzyme. Those elements are linked, or inserted into regions of a native or "optimized" gene under control of a yeast promoter in a vector suitable for expression in *Saccharomyces cerevisiae*. The resulting vectors are then tested for their ability to produce functional desaturase enzymes in strains of Saccharomyces that contain an inactive form of the Δ-9 fatty acid desaturase gene.

In STEP 2, plant desaturase sequences from the above vectors that are found to produce a functional Δ-9 desaturase gene are used to a isolate homologous sequences from plant genomic DNA. The isolated genomic sequences are used to construct a synthetic gene that produces an mRNA that encodes the same functional desaturase protein produced by the vector in step 1. In this instance, the genomic sequences encompass the same protein coding elements as those encoded by the homologous cDNA sequence and also include genomic elements that encode the 5' and/or 3' untranslated regions of the plant desaturase mRNA. These combined genomic elements should differ from the cDNA derived sequences used in STEP 1 by containing authentic plant introns, (which may facilitate efficient and correct splicing of the chimeric mRNA in the plant nucleus) and signals that affect the mRNA stability, mRNA transport, and efficient translation of the mRNA in plant tissues. The chimeric plant/synthetic gene containing the genomic sequences is inserted into vectors under the control of plant seed-specific promoters and tested for expression and desaturase function in plants, including Brassica, Arabidopsis, maize and soybeans.

The following specific examples further illustrate these methods employing the Arabidopsis FAD2 gene, which encodes an ER Δ12-desaturase, as a source of plant desaturase DNA sequences. In the preferred embodiment, the source of the plant desaturase DNA would be the FAD2 homolog, or a related ER lipid biosynthetic gene, that is derived from the same plant species that is intended to be modified by the resulting vector for commercial use.

A. Substitution of the N-terminal OLE1 protein coding sequences and with N-terminal sequences from the derived from the Arabidopsis FAD2 gene.

1) A cDNA containing the FAD2, Δ-12 desaturase, mRNA coding sequence is isolated by reverse transcriptase—polymerase chain reaction (RT-PCR) of isolated mRNAs derived from Arabidopsis tissue or by direct DNA synthesis using the protein and DNA sequences set forth in SEQ ID NO:4 and SEQ ID NO:5 (open reading frame starts at +93).

2) The inventors have shown that substitution of transmembrane sequences of the OLE1 gene with transmembrane sequences from the Saccharomyces FAH2 gene abolishes Δ-9 desaturase activity. FAH2 encodes a sphingolipid fatty acid hydroxylase, which is an ER membrane protein. TMPredict analysis of the Arabidopsis FAD2 sequence indicates that the first transmembrane region of its encoded protein begins at residue +52 and a similar analysis of the OLE1 sequence indicates that its first transmembrane sequence begins at residue +113. Because the inclusion of potential membrane spanning elements from the plant desaturase could produce significant changes in the desaturase core enzyme structure that affect activity, only sequences encoding residues +1 to +52 of FAD2 are tested for functional linkages or substitutions in the 113 residue N-terminal region of OLE1.

A series of PCR oligonucleotide primers are synthesized that include a 5' primer that complements sequences including +1 start codon of the FAD2 gene and 3' primers that complement sequences ending, for example, at residues +20, +35 and +52 of the FAD2 gene. These are used to amplify a series of fragments of different lengths from the FAD2 cDNA that extend from the +1 codon through codon +52. A second PCR amplification is performed using a 5' primer that is complementary to sequences that include the 5' end of the FAD2 mRNA and the 3' primer that includes codon +52. That amplification is done using Arabidopsis genomic DNA as a template. The amplified fragment from that reaction is cloned into a bacterial vector and subjected to DNA sequencing to detect the presence of introns within the genomic sequence. The cloned genomic fragment is also used to construct vectors for plant expression as indicated in STEP 2 of the method.

The amplified cDNA fragments is inserted into yeast expression vectors that contain the native OLE1 mRNA coding sequence under the control of the Saccharomyces galactose inducible, GAL1 promoter. Insertion of the plant DNA fragments can be done in several ways: 1) A fragment is inserted upstream of the OLE1 protein coding sequences so that its protein coding element is fused in frame to the +1 codon of the OLE1 encoded protein, 2) the codons on the plant fragment could replace the equivalent OLE2 residues starting from the +1 ATG codon (e.g. a plant DNA fragment containing codons +1→+52 replaces OLE1 codons +1→+52) and 3) the full length fragment containing codons +1→+52 of the plant gene is fused in frame to codon +114 of the OLE1 gene, replacing the OLE1 residues +1→+113 with plant desaturase residues +1→+52.

The resulting plasmids are transformed into a haploid ole1Δ::LEU2 strain of Saccharomyces. That strain contains a null, disrupted form of the OLE1 gene and therefore has a growth requirement for unsaturated fatty acids. The transformed Saccharomyces strains are grown on fatty acid depleted galactose medium to test for the ability of the induced chimeric gene to support growth of the strain without fatty acids. Transformed strains that grow on the fatty acid deficient medium are further analyzed to assess the effects of the plant sequences on desaturase function. This is done by Western blot analysis, to measure levels of the resulting desaturase protein and by fatty acid analysis of total cellular lipids, to assess the relative activity of the desaturase enzyme by comparison of the ratio of saturated to unsaturated fatty acids.

3) Using information derived from the above tests, a chimeric desaturase gene is constructed using the amplified genomic DNA from the FAD2 gene. Construction, testing, and analysis these vectors is guided by the principle that the most desirable vector is one that maximizes the use of the plant gene sequences and minimizes the use of the Saccharomyces Δ-9 desaturase gene sequences while retaining optimal desaturase function. Plant DNA fragments derived from the genomic DNA amplification that extend from the 5' end of the mRNA sequence to the longest sequence that produces optimal desaturase function in yeast are inserted into a vector containing the native Δ-9 desaturase gene (or one of its modified forms produced by the methods described above). The fragment is inserted into the vector so that the 3' end of its protein coding sequence produces an mRNA that generates a protein sequence identical to its counterpart derived from the FAD2 cDNA sequences. The resulting chimeric desaturase gene, which now encodes an mRNA that includes the FAD2 5' untranslated region in addition to the modified protein coding sequences, is placed into a plant expression vector under the control of a suitable plant promoter and plant termination/polyadenylation sequences.

4) The resulting vectors containing the plant/yeast chimeric desaturase sequences are transformed into plants for testing and analysis of desaturase function. Suitable test plants include *Arabidopsis thaliana*, and *Brassica napis*. A method for transformation and analysis of desaturase gene expression in Arabidopsis is provided above. A method for transformation and analysis of yeast desaturase expression in *Brassica napis* is described in U.S. Pat. No. 5,777,201 to Poutre et al. (incorporated by reference herein).

B. Insertion or substitution of Arabidopsis FAD2 C-terminal protein coding sequences and 3' mRNA untranslated region sequences into native and modified forms of the OLE1 gene.

The inventors have previously shown that proteins encoded by the Saccharomyces ELO2 and ELO3 genes contain a series of charged residues in their C-terminal region. These proteins are located on the ER surface and function in the biosynthesis of very long chain fatty acids as described in Oh et al. (J. Biol. Chem. 272: 17376–17384, 1997) (incorporated by reference herein). They further showed that deletion of the region containing the charged residues causes the proteins to be mislocalized from their normal cellular locations in the endoplasmic reticulum, resulting in reduced function. Similar clusters of charged residues occurs in the C-terminal region of the OLE1 gene that are apparently associated with ER retention or localization. These residues do not appear to be a part of the functional cytochrome $b_5$ domain. A detailed comparison of the C-terminal OLE1 and the Arabidopsis FAD2 sequences show that the plant desaturase has similar, but not identical, clusters of charged residues to those in the OLE1 gene. These sequences are shown below:

SEQ ID Nos: 6 and 7:

Comparison of the charged carboxyl terminal amino acids of Ole1p (SEQ ID NO:7) and the Arabidopsis Fad2p desaturase (SEQ ID NO:6) (The region of the OLE1 gene shown does not appear to be a functional part of its cytochrome $b_5$ domain).

```
                +- + -    - -+-   -++        +
A. thaliana  WYVAMYREAK ECIYVEPDRE GDKKGVYWYN NKL*
FAD2

+- +    +   ++    - - +
S. cerevisiae MRVAVIKESK NSAIRMASKR GEIYETGKFF *
OLE1
```

Methods similar to those shown in Section A can be used to identify Arabidopsis FAD2 sequences that can replace the OLE1 C-terminal sequences to optimize gene expression, membrane targeting and ER retention of the chimeric enzyme.

1) A series of oligonucleotide primers for PCR amplification are synthesized for isolation of elements in the C-terminal region of the FAD2 gene. A FAD2 DNA fragment encompassing that region is generated by PCR amplification of the cDNA clone. Alternatively, given the smaller size of the fragment it or modified forms of the plant fragment may be generated directly by DNA synthesis. A fragment containing that region and its flanking 3' untranslated region also is generated by PCR amplification of Arabidopsis genomic DNA as described above. That fragment is cloned into an appropriate vector and sequenced. as also described.

2) Vectors are constructed that contain the plant DNA fragments linked to or substituted into the OLE1 C-terminal coding region as described in Section A. In this instance, the plant DNA fragments are linked in frame to the carboxyl terminal residues of the OLE1 protein coding region.

3) The resulting vectors are transformed into the Saccharomyces ole1Δ strain and tested for desaturase function as described in Section A.

4) Using information derived from the above tests, chimeric desaturase genes containing the C-terminal plant sequences that produce functional desaturases are constructed using the amplified genomic DNA from the FAD2 gene, according to the principles outlined in Section A. The resulting sequences are employed to construct vectors that will express the chimeric plant/yeast gene under control of plant promoter and plant termination/polyadenylation sequences. Those vectors are transformed into plants for testing and analysis of desaturase function as described above.

The present invention is not limited to the embodiments described and exemplified above, but is capable of variation and modification without departure from the scope of the appended claims.

We claim:

1. A synthetic fatty acid desaturase gene for expression in a multicellular plant, the gene comprising SEQ ID NO:3, wherein the gene is customized from a naturally occurring cytosolic Δ-9 desaturase gene from *Saccharomyces cerevisiae* for expression in a plant cytoplasm.

2. The synthetic gene of claim 1, which further comprises an expression regulatory sequence from a plant gene encoding an ER biosynthetic pathway enzyme.

3. The synthetic gene of claim 1, customized for expression in a monocotyledonous plant.

4. The synthetic gene of claim 1, customized for expression in a dicotyledonous plant.

5. The synthetic gene of claim 1, customized for expression in a plant genus selected from the group consisting of Arabidopsis, Brassica, Phaseolus, Oryza, Olea, Elaeis (Oil Palm) and Zea.

6. The synthetic gene of claim 1, customized from a naturally occurring gene comprising both a desaturase domain and a cyt $b_5$ domain.

7. The synthetic gene of claim 1, wherein the gene is a chimeric gene comprising a desaturase domain and a heterologous cyt $b_5$ domain.

8. The synthetic gene of claim 1, customized from a naturally occurring gene such that the synthetic gene and the naturally occurring gene encode an identical amino acid sequence.

9. The synthetic gene of claim 8, wherein the synthetic gene and the naturally occurring gene encode SEQ ID NO:2.

10. The synthetic gene of claim 1, customized from a naturally occurring gene such that the synthetic gene and the naturally occurring gene encode a similar amino acid sequence.

11. The synthetic gene of claim 1, customized from a naturally occurring gene such that the synthetic gene and the naturally occurring gene encode a similar amino acid sequence, and the synthetic gene possesses improved stability or catalytic activity as compared with the naturally occurring gene.

* * * * *

SEQUENCE LISTING

<160> NUMBER OF SEQ ID NOS: 8

<210> SEQ ID NO 1
<211> LENGTH: 1555
<212> TYPE: DNA

<213> ORGANISM: Saccharomyces cerevisiae

<400> SEQUENCE: 1

| | | | | | |
|---|---|---|---|---|---|
| tacaacaaag | atgccaactt | ctggaactac | tattgaattg | attgacgacc | aatttccaaa | 60 |
| ggatgactct | gccagcagtg | gcattgtcga | cgaagtcgac | ttaacggaag | ctaatatttt | 120 |
| ggctactggt | ttgaataaga | aagcaccaag | aattgtcaac | ggttttggtt | ctttaatggg | 180 |
| ctccaaggaa | atggtttccg | tggaattcga | caagaaggga | aacgaaaaga | agtccaattt | 240 |
| ggatcgtctg | ctagaaaagg | acaaccaaga | aaaagaagaa | gctaaaacta | aaattcacat | 300 |
| ctccgaacaa | ccatggactt | tgaataactg | gcaccaacat | ttgaactggt | tgaacatggt | 360 |
| tcttgtttgt | ggtatgccaa | tgattggttg | gtacttcgct | ctctctggta | agtaccttt | 420 |
| gcatttaaac | gttttccttt | tctccgtttt | ctactacgct | gtcggtggtg | tttctattac | 480 |
| tgccggttac | catagattat | ggtctcacag | atcttactcc | gctcactggc | cattgagatt | 540 |
| attctacgct | atcttcggtt | gtgcttccgt | tgaagggtcc | gctaaatggt | ggggccactc | 600 |
| tcacagaatt | caccatcgtt | acactgatac | cttgagagat | ccttatgacg | ctcgtagagg | 660 |
| tctatggtac | tcccacatgg | gatggatgct | tttgaagcca | aatccaaaat | acaaggctag | 720 |
| agctgatatt | accgatatga | ctgatgattg | gaccattaga | ttccaacaca | gacactacat | 780 |
| cttgttgatg | ttattaaccg | ctttcgtcat | tccaactctt | atctgtggtt | acttttcaa | 840 |
| cgactatatg | ggtggtttga | tctatgccgg | ttttattcgt | gtctttgtca | ttcaacaagc | 900 |
| taccttttgc | attaactcca | tggctcatta | catcggtacc | caaccattcg | atgacagaag | 960 |
| aaccccctcgt | gacaactgga | ttactgccat | tgttactttc | ggtgaaggtt | accataactt | 1020 |
| ccaccacgaa | ttcccaactg | attacagaaa | cgctattaag | tggtaccaat | acgacccaac | 1080 |
| taaggttatc | atctatttga | cttctttagt | tggtctagca | tacgacttga | agaaattctc | 1140 |
| tcaaaatgct | attgaagaag | ccttgattca | acaagaacaa | agaagatca | ataaaaagaa | 1200 |
| ggctaagatt | aactggggtc | cagttttgac | tgatttgcca | atgtgggaca | acaaacctt | 1260 |
| cttggctaag | tctaaggaaa | acaagggttt | ggttatcatt | tctggtattg | ttcacgacgt | 1320 |
| atctggttat | atctctgaac | atccaggtgg | tgaaactta | attaaaactg | cattaggtaa | 1380 |
| ggacgctacc | aaggctttca | gtggtggtgt | ctaccgtcac | tcaaatgccg | ctcaaaatgt | 1440 |
| cttggctgat | atgagagtgg | ctgttatcaa | ggaaagtaag | aactctgcta | ttagaatggc | 1500 |
| tagtaagaga | ggtgaaatct | acgaaactgg | taagttcttt | taagcatcac | attac | 1555 |

<210> SEQ ID NO 2
<211> LENGTH: 510
<212> TYPE: PRT
<213> ORGANISM: Saccharomyces cerevisiae

<400> SEQUENCE: 2

Met Pro Thr Ser Gly Thr Thr Ile Glu Leu Ile Asp Asp Gln Phe Pro
1               5                   10                  15

Lys Asp Asp Ser Ala Ser Ser Gly Ile Val Asp Glu Val Asp Leu Thr
            20                  25                  30

Glu Ala Asn Ile Leu Ala Thr Gly Leu Asn Lys Lys Ala Pro Arg Ile
        35                  40                  45

Val Asn Gly Phe Gly Ser Leu Met Gly Ser Lys Glu Met Val Ser Val
    50                  55                  60

Glu Phe Asp Lys Lys Gly Asn Glu Lys Lys Ser Asn Leu Asp Arg Leu
65                  70                  75                  80

```
Leu Glu Lys Asp Asn Gln Glu Lys Glu Ala Lys Thr Lys Ile His
                85                  90                  95

Ile Ser Glu Gln Pro Trp Thr Leu Asn Asn Trp His Gln His Leu Asn
               100                 105                 110

Trp Leu Asn Met Val Leu Val Cys Gly Met Pro Met Ile Gly Trp Tyr
               115                 120                 125

Phe Ala Leu Ser Gly Lys Val Pro Leu His Leu Asn Val Phe Leu Phe
           130                 135                 140

Ser Val Phe Tyr Tyr Ala Val Gly Val Ser Ile Thr Ala Gly Tyr
145                 150                 155                 160

His Arg Leu Trp Ser His Arg Ser Tyr Ser Ala His Trp Pro Leu Arg
               165                 170                 175

Leu Phe Tyr Ala Ile Phe Gly Cys Ala Ser Val Glu Gly Ser Ala Lys
           180                 185                 190

Trp Trp Gly His Ser His Arg Ile His His Arg Tyr Thr Asp Thr Leu
195                 200                 205

Arg Asp Pro Tyr Asp Ala Arg Arg Gly Leu Trp Tyr Ser His Met Gly
           210                 215                 220

Trp Met Leu Leu Lys Pro Asn Pro Lys Tyr Lys Ala Arg Ala Asp Ile
225                 230                 235                 240

Thr Asp Met Thr Asp Asp Trp Thr Ile Arg Phe Gln His Arg His Tyr
               245                 250                 255

Ile Leu Leu Met Leu Leu Thr Ala Phe Val Ile Pro Thr Leu Ile Cys
               260                 265                 270

Gly Tyr Phe Phe Asn Asp Tyr Met Gly Gly Leu Ile Tyr Ala Gly Phe
           275                 280                 285

Ile Arg Val Phe Val Ile Gln Gln Ala Thr Phe Cys Ile Asn Ser Leu
           290                 295                 300

Ala His Tyr Ile Gly Thr Gln Pro Phe Asp Asp Arg Arg Thr Pro Arg
305                 310                 315                 320

Asp Asn Trp Ile Thr Ala Ile Val Thr Phe Gly Glu Gly Tyr His Asn
               325                 330                 335

Phe His His Glu Phe Pro Thr Asp Tyr Arg Asn Ala Ile Lys Trp Tyr
           340                 345                 350

Gln Tyr Asp Pro Thr Lys Val Ile Ile Tyr Leu Thr Ser Leu Val Gly
           355                 360                 365

Leu Ala Tyr Asp Leu Lys Lys Phe Ser Gln Asn Ala Ile Glu Glu Ala
    370                 375                 380

Leu Ile Gln Gln Glu Gln Lys Lys Ile Asn Lys Lys Ala Lys Ile
385                 390                 395                 400

Asn Trp Gly Pro Val Leu Thr Asp Leu Pro Met Trp Asp Lys Gln Thr
               405                 410                 415

Phe Leu Ala Lys Ser Lys Glu Asn Lys Gly Leu Val Ile Ile Ser Gly
           420                 425                 430

Ile Val His Asp Val Ser Gly Tyr Ile Ser Glu His Pro Gly Gly Glu
    435                 440                 445

Thr Leu Ile Lys Thr Ala Leu Gly Lys Asp Ala Thr Lys Ala Phe Ser
450                 455                 460

Gly Gly Val Tyr Arg His Ser Asn Ala Ala Gln Asn Val Leu Ala Asp
465                 470                 475                 480

Met Arg Val Ala Val Ile Lys Glu Ser Lys Asn Ser Ala Ile Arg Met
               485                 490                 495

Ala Ser Lys Arg Gly Glu Ile Tyr Glu Thr Gly Lys Phe Phe
```

-continued

<210> SEQ ID NO 3
<211> LENGTH: 1555
<212> TYPE: DNA
<213> ORGANISM: Artificial Sequence
<220> FEATURE:
<223> OTHER INFORMATION: synthetic yeast delta-9 desaturase gene modified for expression in plants

<400> SEQUENCE: 3

```
ggatccaaca atgcctactt ctggaactac tatcgagctt atcgatgatc aattccctaa        60
ggatgattct gcttcttctg gaatcgttga tgaggttgat cttactgagg ctaacatcct       120
tgctactgga cttaacaaga aggctcctag aatcgttaac ggattcggat ctcttatggg       180
atctaaggag atggtttctg ttgagttcga taagaaggga acgagaaga agtctaacct        240
tgatagactt cttgagaagg ataaccaaga gaaggaggag gctaagacta agatccatat       300
ctctgagcaa ccttggactc tcaacaactg gcatcaacat ctcaactggc tcaacatggt       360
gctcgtctgt ggaatgccta tgatcggatg gtacttcgct ctctctggaa aagtgcctct       420
ccatctcaac gttttcctct tctctgtctt ctactacgct gttggaggag tgtctatcac       480
tgctggatac catagactct ggtctcatag atcttactct gctcattggc tcttagact         540
cttctacgct atctttggat gtgcttctgt tgagggatct gctaagtggt ggggacattc       600
tcatagaatc catcatagat acactgatac tcttagagat ccttacgatg ctagaagagg       660
actttggtac tctcatatgg gatggatgct tcttaagcct aaccctaagt acaaggctag       720
agctgatatc actgatatga ctgatgattg gactatcaga ttccaacata gacattacat       780
cttgctcatg ctccttactg cttctcgtgat cctactctc atctgtggat acttcttcaa       840
cgattacatg ggaggactca tctacgctgg attcatcaga gtgttcgtca tccaacaagc       900
tactttctgt atcaactcta tggctcatta catcggaact caacctttcg atgatagaag       960
aactcctaga gataactgga tcactgctat cgttactttc ggagagggat accataactt      1020
ccatcatgag ttccctactg attatagaaa cgctatcaag tggtaccaat acgatcctac      1080
taaagtgatc atctacttga cttctctcgt gggacttgct tacgatctca agaagttctc      1140
tcaaaacgct atcgaggagg ctcttatcca acaagagcaa aagaagatca acaagaagaa      1200
ggctaagatt aattggggac tgttcttac tgatcttcct atgtgggata agcaaacttt       1260
ccttgctaag tctaaggaga acaagggact tgttatcatc tctggaatcg ttcatgatgt      1320
ttctggatac atctctgagc atcctggagg agagacttta attaagactg ctcttggaaa      1380
ggatgctact aaggctttct ctggaggagt ttacagacat tctaacgctg ctcaaaacgt      1440
gcttgctgat atgagagttg ctgttatcaa ggagtctaag aactctgcta tcagaatggc      1500
ttctaagaga ggagagatct acgagactgg aaagttcttc tgatctagag gatcc          1555
```

<210> SEQ ID NO 4
<211> LENGTH: 383
<212> TYPE: PRT
<213> ORGANISM: Arabidopsis thaliana

<400> SEQUENCE: 4

Met Gly Ala Gly Gly Arg Met Pro Val Pro Thr Ser Ser Lys Lys Ser
 1               5                   10                  15

Glu Thr Asp Thr Thr Lys Arg Val Pro Cys Glu Lys Pro Pro Phe Ser
             20                  25                  30

-continued

| | | | | | | | | | | | |
|---|---|---|---|---|---|---|---|---|---|---|---|
|Val|Gly|Asp|Leu|Lys|Lys|Ala|Ile|Pro|Pro|His|Cys|Phe|Lys|Arg|Ser
| | |35| | | |40| | | |45| |

Ile Pro Arg Ser Phe Ser Tyr Leu Ile Ser Asp Ile Ile Ala Ser
    50                  55                  60

Cys Phe Tyr Tyr Val Ala Thr Asn Tyr Phe Ser Leu Leu Pro Gln Pro
65                      70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
                100              105              110

Ser Asp Tyr Gln Trp Leu Asp Asp Thr Val Gly Leu Ile Phe His Ser
            115              120              125

Phe Leu Leu Val Pro Tyr Phe Ser Trp Lys Tyr Ser His Arg Arg His
    130                135              140

His Ser Asn Thr Gly Ser Leu Glu Arg Asp Glu Val Phe Val Pro Lys
145                    150              155                160

Gln Lys Ser Ala Ile Lys Trp Tyr Gly Lys Tyr Leu Asn Asn Pro Leu
                165              170              175

Gly Arg Ile Met Met Leu Thr Val Gln Phe Val Leu Gly Trp Pro Leu
                180              185              190

Tyr Leu Ala Phe Asn Val Ser Gly Arg Pro Tyr Asp Gly Phe Ala Cys
        195              200              205

His Phe Phe Pro Asn Ala Pro Ile Tyr Asn Asp Arg Glu Arg Leu Gln
    210                215              220

Ile Tyr Leu Ser Asp Ala Gly Ile Leu Ala Val Cys Phe Gly Leu Tyr
225                    230              235                240

Arg Tyr Ala Ala Ala Gln Gly Met Ala Ser Met Ile Cys Leu Tyr Gly
                245              250              255

Val Pro Leu Leu Ile Val Asn Ala Phe Leu Val Leu Ile Thr Tyr Leu
            260              265              270

Gln His Thr His Pro Ser Leu Pro His Tyr Asp Ser Ser Glu Trp Asp
        275              280              285

Trp Leu Arg Gly Ala Leu Ala Thr Val Asp Arg Asp Tyr Gly Ile Leu
    290                295              300

Asn Lys Val Phe His Asn Ile Thr Asp Thr His Val Ala His His Leu
305                    310              315                320

Phe Ser Thr Met Pro His Tyr Asn Ala Met Glu Ala Thr Lys Ala Ile
                325              330              335

Lys Pro Ile Leu Gly Asp Tyr Tyr Gln Phe Asp Gly Thr Pro Trp Tyr
            340              345              350

Val Ala Met Tyr Arg Glu Ala Lys Glu Cys Ile Tyr Val Glu Pro Asp
        355              360              365

Arg Glu Gly Asp Lys Lys Gly Val Tyr Trp Tyr Asn Asn Lys Leu
    370                375              380

<210> SEQ ID NO 5
<211> LENGTH: 1372
<212> TYPE: DNA
<213> ORGANISM: Arabidopsis thaliana

<400> SEQUENCE: 5
agagagagag attctgcgga ggagcttctt cttcgtaggg tgttcatcgt tattaacgtt    60
atcgccccta cgtcagctcc atctccagaa acatgggtgc aggtggaaga atgccggttc   120
ctacttcttc caagaaatcg gaaaccgaca ccacaaagcg tgtgccgtgc gagaaaccgc   180

```
                                                        -continued cttctcggt gggagatctg aagaaagcaa tcccgccgca ttgtttcaaa cgctcaatcc    240
ctcgctcttt ctcctacctt atcagtgaca tcattatagc ctcatgcttc tactacgtcg    300
ccaccaatta cttctctctc ctccctcagc ctctctctta cttggcttgg ccactctatt    360
gggcctgtca aggctgtgtc ctaactggta tctgggtcat agcccacgaa tgcggtcacc    420
acgcattcag cgactaccaa tggctggatg acacagttgg tcttatcttc cattccttcc    480
tcctcgtccc ttacttctcc tggaagtata gtcatcgccg tcaccattcc aacactggat    540
ccctcgaaag agatgaagta tttgtcccaa agcagaaatc agcaatcaag tggtacggga    600
aatacctcaa caaccctctt ggacgcatca tgatgttaac cgtccagttt gtcctcgggt    660
ggcccttgta cttagccttt aacgtctctg cagaccgta tgacgggttc gcttgccatt    720
tcttccccaa cgctcccatc tacaatgacc gagaacgcct ccagatatac ctctctgatg    780
cgggtattct agccgtctgt tttggtcttt accgttacgc tgctgcacaa gggatggcct    840
cgatgatctg cctctacgga gtaccgcttc tgatagtgaa tgcgttcctc gtcttgatca    900
cttacttgca gcacactcat ccctcgttgc ctcactacga ttcatcagag tgggactggc    960
tcaggggagc tttggctacc gtagacagag actacgaaat cttgaacaag gtgttccaca   1020
acattacaga cacacacgtg gctcatcacc tgttctcgac aatgccgcat tataacgcaa   1080
tggaagctac aaaggcgata aagccaattc tgggagacta ttaccagttc gatggaacac   1140
cgtggtatgt agcgatgtat agggaggcaa aggagtgtat ctatgtagaa ccggacaggg   1200
aaggtgacaa gaaaggtgtg tactggtaca acaataagtt atgagcatga tggtgaagaa   1260
attgtcgacc tttctcttgt ctgtttgtct tttgttaaag aagctatgct tcgttttaat   1320
aatcttattg tccattttgt tgtgttatga cattttggct gctcattatg tt           1372
```

<210> SEQ ID NO 6
<211> LENGTH:
<212> TYPE:
<213> ORGANISM:

<400> SEQUENCE: 6

000

<210> SEQ ID NO 7
<211> LENGTH: 33
<212> TYPE: PRT
<213> ORGANISM: Arabidopsis thaliana

<400> SEQUENCE: 7

Trp Tyr Val Ala Met Tyr Arg Glu Ala Lys Glu Cys Ile Tyr Val Glu
 1               5                  10                  15

Pro Asp Arg Glu Gly Asp Lys Lys Gly Val Tyr Trp Tyr Asn Asn Lys
            20                  25                  30

Leu

<210> SEQ ID NO 8
<211> LENGTH: 30
<212> TYPE: PRT
<213> ORGANISM: Saccharomyces cerevisiae

<400> SEQUENCE: 8

-continued

```
Met Arg Val Ala Val Ile Lys Glu Ser Lys Asn Ser Ala Ile Arg Met
 1               5                  10                  15

Ala Ser Lys Arg Gly Glu Ile Tyr Glu Thr Gly Lys Phe Phe
             20                  25                  30
```